United States Patent
Lim et al.

(10) Patent No.: US 7,338,936 B2
(45) Date of Patent: *Mar. 4, 2008

(54) USE OF ANTIMICROBIAL PROTEINS AND PEPTIDES FOR THE TREATMENT OF OTITIS MEDIA AND PARANASAL SINUSITIS

(75) Inventors: David J. Lim, Pasadena, CA (US); Haa-Yung Lee, La Crescenta, CA (US); Paul Webster, Pasadena, CA (US); Ali Andalibi, Altadena, CA (US); Jian-Dong Li, Glendale, CA (US); Tomas Ganz, Los Angeles, CA (US); Kiweon Cha, Irvine, CA (US)

(73) Assignee: House Ear Institute, Los Angeles, CA (US)

( * ) Notice: Subject to any disclaimer, the term of this patent is extended or adjusted under 35 U.S.C. 154(b) by 115 days.

This patent is subject to a terminal disclaimer.

(21) Appl. No.: 10/971,559

(22) Filed: Oct. 22, 2004

(65) Prior Publication Data

US 2006/0034820 A1    Feb. 16, 2006

Related U.S. Application Data

(63) Continuation-in-part of application No. 10/819,714, filed on Apr. 6, 2004, now Pat. No. 7,060,674, which is a continuation of application No. 09/998,547, filed on Nov. 27, 2001, now Pat. No. 6,716,813.

(60) Provisional application No. 60/253,492, filed on Nov. 28, 2000.

(51) Int. Cl.
*A61K 38/17* (2006.01)
*C07K 14/435* (2006.01)

(52) U.S. Cl. .......................... 514/12; 530/324
(58) Field of Classification Search ................ 514/12; 530/324
See application file for complete search history.

(56) References Cited

U.S. PATENT DOCUMENTS

| | | | |
|---|---|---|---|
| 4,705,777 A | | 11/1987 | Lehrer et al. |
| 5,200,182 A | * | 4/1993 | Kiczka ...................... 424/94.5 |
| 5,719,196 A | * | 2/1998 | Uhari et al. ................ 514/738 |
| 5,849,490 A | | 12/1998 | Schonwetter et al. |
| 5,942,217 A | | 8/1999 | Woo et al. |
| 6,335,318 B1 | | 1/2002 | Selsted et al. |
| 2003/0176652 A1 | * | 9/2003 | McCray et al. ............ 530/350 |
| 2004/0072777 A1 | * | 4/2004 | Froelich et al. ............ 514/44 |

OTHER PUBLICATIONS

Lehrer et al., "Antimicrobial peptides in mammalian and insect host defence," Curr Opin Immunol 11:23-27, 1999.*
Singh et al., "Synergistic and additive killing by antimicrobial factors found in human airway surface liquid," Am J Physiol Lung Cell Mol Physiol 279:L799-L805, 2000.*

(Continued)

*Primary Examiner*—Jon Weber
*Assistant Examiner*—Rosanne Kosson
(74) *Attorney, Agent, or Firm*—Knobbe, Martens, Olson & Bear LLP

(57) ABSTRACT

The pharmaceutical composition and a method of treatment of infectious diseases, such as otitis media, paranasal sinusitis, labyrinthitis and meningitis are described. The composition comprises EP2E or homologues thereof.

15 Claims, 21 Drawing Sheets

OTHER PUBLICATIONS

Hanamure et al., "Normal distribution of lysozyme- and lactoferrin-secreting cells in the chinchilla tubotympanum," Am J Otolaryngal 4:410-425, 1986.*

Aebi, C., et al. (1996) Expression of the CopB Outer Membrane Protein by *Moraxella catarrhalis* Is Regulated by Iron and Affects Iron Acquisition from Transferrin and Lactoferrin. Infect. Immun. 64(6):2024-2030.

Arnold, R. R., et al. (1982) Bactericidal Activity of Human Lactoferrin: Differentiation from the Stasis of Iron Deprivation. Infect. Immun. 35(3):792-799.

Arnold, R. R., et al. (1977) A Bactericidal Effect for Human Lactoferrin. Science. 197:263-265.

Bals, R., et al. (1998) Human β-Defensin 2 is a Salt-Sensitive Peptide Antibiotic Expressed in Human Lung. J. Clin. Invest. 102:874-880.

Bals, R., et al. (1998) Mouse β-Defensin 1 Is a Salt-Sensitive Antimicrobial Peptide Present in Epithelia of the Lung and Urogenital Tract. Infect. Immun. 66(3):1225-1232.

Bernstein, J. M. & Ogra, P. L. (1980) Mucosal immune system: implications in otitis media with effusion. Ann. Otol. Rhinol. Laryngol. Suppl. 89(Suppl 68):326-332.

Block, S. L. (1997) Causative pathogens, antibiotic resistance and therapeutic considerations in acute otitis media. Pediatr. Infect. Dis. J. 16:449-456.

Bluestone, C. D. and Klein, J. O. (1995) Otitis Media in Infants and Children, 2nd Edition, W.B. Saunders Company, Philadelphia, table of contents only.

Boe, R., et al. (1999) Human β-defensin-1 mRNA Is Transcribed in Tympanic Membrane and Adjacent Auditory Canal Epithelium. Infect. Immun. 67(9):4843-4846.

Bonnah, R. A., et al. (1998) Biochemical and immunological properties of lactoferrin binding proteins from *Moraxella (Branhamella) catarrhalis*. Microb. Pathog. 24:89-100.

Bowes, D. & Corrin, B. (1977) Ultrastructural immunocytochemical localisation of lysozyme in human bronchial glands. Thorax. 32:163-170.

Brook, I. (1994) Otitis Media: Microbiology and Management. J. Otolaryngol. 23(4):269-275.

Campagnari, A. A., et al. (1994) Growth of *Moraxella catarrhalis* with Human Transferrin and Lactoferrin: Expression of Iron-Repressible Proteins Without Siderophore Production. Infect. Immun. 62(11):4909-14.

Chartrand, S. A. & Pong, A. (1998) Acute Otitis Media in the 1990s: The Impact of Antibiotic Resistance. Pediatr. Ann. 27(2):86-95.

Ellison, R. T., III (1994) The effects of lactoferrin on gram-negative bacteria. Adv. Exp. Med. Biol. 357:71-90.

Ganz, T. & Lehrer, R. I. (1995) Defensins. Pharmacol. Ther. 66:191-205.

Ganz, T. & Lehrer, R. I. (1998) Antimicrobial peptides of vertebrates. Curr. Opin. Immunol. 10:41-44.

Garcia, J. R., et al. (2001) Human β-defensin 4: a novel inducible peptide with a specific salt-sensitive spectrum of antimicrobial activity. FASEB J. 15:1819-21.

Goldoni, P., et al. (2000) Metal complexes of lactoferrin and their effect on the intracellular multiplication of *Legionella pneumophila*. Biometals 13:15-22.

Hanamure, Y. & Lim, D. J. (1986) Normal Distribution of Lysozyme- and Lactoferrin-secreting Cells in the Chinchilla Tubotympanum. Am. J. Otolaryngol. 4:410-425.

Harder, J., et al. (2001) Isolation and Characterization of Human β-Defensin-3, a Novel Human Inducible Peptide Antibiotic. J. Biol. Chem. 276(8):5707-1713.

Hiratsuka, T., et al. (1998) Identification of Human β-Defensin-2 in Respiratory Tract and Plasma and Its Increase in Bacterial Pneumonia. Biochem. Biophys. Res. Commun. 249:943-947.

Hoppe, H. L. & Johnson, C. E. (1998) Otitis media: Focus on antimicrobial resistance and new treatment options. Am. J. Health Syst. Pharm. 55(18):1881-1897.

Jia, H. P., et al. (2001) Discovery of new human β-defensins using a genomics-based approach. Gene 263:211-218.

Lehrer, R. I., et al. (1991) Ultrasensitive assays for endogenous antimicrobial polypeptides. J. Immunol. Methods 137:167-173.

Lehrer, R. I. & Ganz, T. (1999) Antimicrobial peptides in mammalian and insect host defence. Curr. Opin. Immunol. 11:23-27.

Leitch, E. C. & Willcox, M. D. (1998) Synergic antistaphylococcal properties of lactoferrin and lysozyme. J. Med. Microbiol. 47:837-842.

Lim, D. J., et al. (2000) Cell biology of tubotympanum in relation to pathogenesis of otitis media—a review, Vaccine 19(Suppl 1):S17-S25.

Miyasaki, K. T., et al. (1990) In Vitro Sensitivity of Oral, Gram-Negative, Facultative Bacteria to the Bactericidal Activity of Human Neutrophil Defensins. Infect. Immun. 58(12):3934-3940.

Muhle, S. A. & Tam, J. P. (2001) Design of Gram-Negative Selective Antimicrobial Peptides. Biochemistry 2001 40:5777-5785.

O'Neil, D. A., et al. (1999) Expression and Regulation of the Human β-Defensins hBD-1 and hBD-2 in Intestinal Epithelium. J. Immunol. 163:6718-6724.

Pierce, A., et al. (1997) Lactoferrin Almost Absent From Lactating Rat Mammary Gland Is Replaced by Transferrin. In Lactoferrin: Interactions and Biological Functions (Eds. Hutchens, T. W. & Lonnerdal, B.) 124-134 (Humana Press, Totowa, New Jersey).

Plaut, A. G., et al. (2000) Human lactoferrin proteolytic activity: analysis of the cleaved region in the IgA protease of *Haemophilus influenzae*. Vaccine. 19(Suppl 1):S148-S152.

Prellner, K., et al. (1984) Pneumococcal antibodies and complement during and after periods of recurrent otitis. Int. J. Pediatr. Otorhinolaryngol. 7:39-49.

Qiu, J., et al. (1998) Human milk lactoferrin inactivates two putative colonization factors expressed by *Haemophilus influenzae*. PNAS 95:12641-12646.

Schroder, J. M. & Harder, J. (1999) Human beta-defensin-2. Int. J. Biochem. Cell Biol. 31:645-51.

Selsted et al. (1993) The Journal of Biological Chemistry 268(9):6641-6648.

Shimoda, M., et al. (1995) Morphology of Defensin-Treated *Staphylococcus aureus*. Infect. Imun. 63(8):2886-2891.

Singh, P. K., et al. (1998) Production of β-defensins by human airway epithelia. PNAS 95:14961-14966.

Singh P. K., et al. (2000) Synergistic and additive killing by antimicrobial factors found in human airway surface liquid. Am. J. Physiol. Lung Cell Mol. Physiol. 279: L799-L805.

Takemura, H., et al. (1996) Evaluation of Susceptibility of Gram-Positive and -Negative Bacteria to Human Defensins by Using Radial Diffusion Assay, Antimicrob. Agents Chemother. 40(10):2280-2284.

Tam, J. P., et al. (2000) Marked Increase in Membranolytic Selectivity of Novel Cyclic Tachyplesins Constrained with an Antiparallel Two-β Strand Cystine Knot Framework. Biochem. Biophys. Res. Commun. 267(3):783-790.

Yu, Q., et al. (2000) Engineered Salt-insensitive α-defensins with End-to-end Circularized Structures. J. Biol. Chem. 276(6):3943-3949.

* cited by examiner

| Gene | Chr location | Gene type | Amino acid sequence of six-cysteine domain |
|---|---|---|---|
| | | | 1  2  3  4  56 |
| DEFB1 | 8p23-p22 | K | YNCVS--SGGQCLYSACPIFTKIQTCYR-GRAKCCK |
| DEFB2 | 8p23-p22 | K | VTCLK--SGAICHPVFCPRRYKQIGTCGL-PGTKCCKKP |
| DEFBp1 | 8p23-p22 | S | *CVLNVCSTSLRQIGTYGR-DRICCRR |
| DEFB3 | 8p23-p22 | K | YYCRV--RGGRCAVLSCLPKEEQIGKCST-RGRKCCRRKK |
| DEFB4 | 8p23-p22 | K | RICGY--GTARCRKK-CRSQEYRIGRCPN--TYACCLRK |
| DEFB5 | 8p23-p22 | P | ESCKL--GRGKCRKE-CLENEKPDGNCRKL--NFLCCRQRI |
| DEFB6 | 8p23-p22 | R | EKCNK--LKGTCKNN-CGKNEELIALCQK--SLKCCKTIQPC+5 |
| DEFB7 | 8p23-p22 | P | TNC (+21)   CEAE-CLTFEVKIGGCRAELAPFCCKNRKAK |
| DEFB8 | 8p23-p22 | P | EICER--PNGSCRDF-CLETEIHVGRCLN--SRPCCLPLGHQ+11 |
| DEFB9 | 8p23-p22 | P | GHCLN--LSGVCRRDVCKVVEDQIGACRKK--RMKCCRAWWIL+21 |
| SPAG11 (EP2E) | 8p23-p22 | R | VDCRR--SEGFCQEY-CNYMETQVGYCSK--KRDACCLR |
| | 8p23-p22 | R | TICRM--QQCICRLFFCRSGEKKRDICSD-PWNRCCVSNTDE |
| DEFB31 | A | P | DECPS--EYYHCRLK-CNADEHAIRYCAD--FSICCKLKI |
| Consensus | | | ++Cxx---xxGxC++x--C+xxE++xIxxCxx---x+.CC |

Fig. 11

SPAG11
(EP2E)
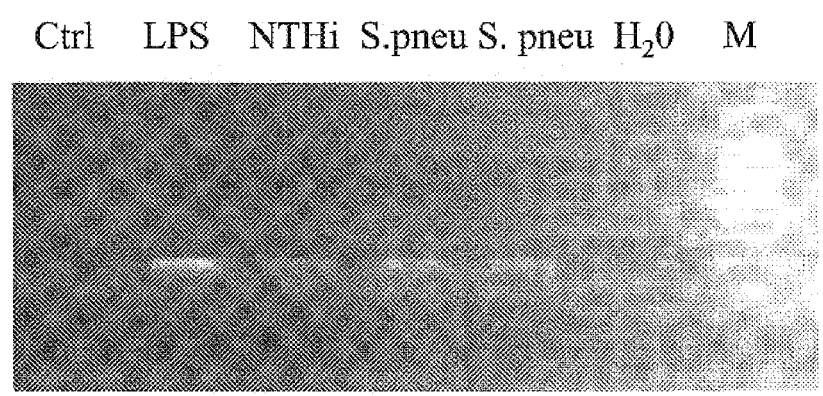
18S
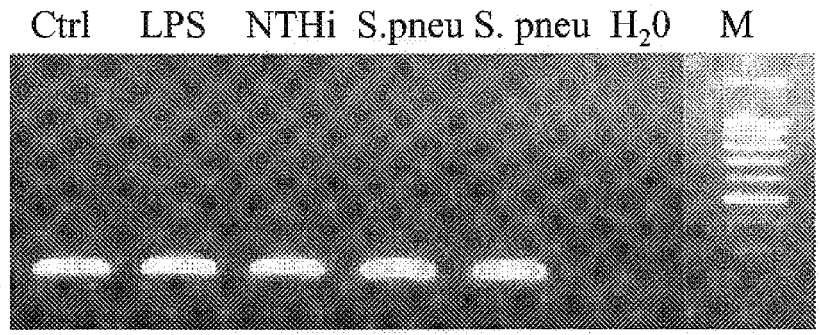
Fig. 13

USE OF ANTIMICROBIAL PROTEINS AND PEPTIDES FOR THE TREATMENT OF OTITIS MEDIA AND PARANASAL SINUSITIS

RELATED APPLICATIONS

This application is a continuation-in-part of the U.S. application Ser. No. 10/819,714 filed Apr. 6, 2004, now U.S. Pat. No. 7,060,674, which is a continuation of U.S. application Ser. No. 09/998,547 filed Nov. 27, 2001, now U.S. Pat. No. 6,716,813, which claims the benefit of U.S. Provisional Application No. 60/253,492 filed Nov. 28, 2000, all of which are expressly incorporated herein by reference in their entireties.

BACKGROUND OF THE INVENTION

1. Field of the Invention

The invention relates generally to the use of human beta defensins, lysozyme, and lactoferrin as a new class of non-antibiotic antimicrobials. More specifically, the invention relates to the use of these antimicrobials for the treatment of otitis media and paranasal sinusitis.

2. Description of the Related Art

The rapid worldwide increase in antibiotic resistance among pathogens has given rise to an urgent need to develop new and innovative non-antibiotic approaches to prevent and manage disease. Otitis media (OM) and sinusitis are two very common infections which are difficult to treat for a number of reasons, including antibiotic resistance. OM is the most prevalent infectious disease affecting young children, and the major cause of conductive hearing loss among this group. OM is also the leading indication for antibiotic therapy. OM results in 31 million annual visits to physicians' offices and is estimated to have a yearly cost exceeding $5 billion.

OM occurs along a continuum. For example, OM with effusion characterized by fluid pathology can lead to chronic OM plus chronic mastoiditis, characterized by the presence of intractable tissue pathology such as cholesteatoma, cholesterol granuloma or granulation tissue. The literature defines chronic OM as having a tympanic membrane perforation and otorrhea. Amongst many other sequelae, which can result from the continuum, an important common one is chronic silent OM. This overlooked entity which includes pathology beneath an intact tympanic membrane is commonly seen in patients. Labyrinthitis is the most frequent complication of chronic OM.

Most cases of OM are caused by one of three major pathogens, *Streptococcus pneumoniae* (*S. pneumoniae*) (30-40%), non-typeable *Haemophilus influenzae* (NTHi) (30%) and *Moraxella catarrhalis* (*M. catarrhalis*) (20%). These are the same pathogens that can also cause meningitis. Typically, these infections are treated with antibiotics. In the past three decades, there has been a dramatic worldwide increase in antibiotic resistance in OM pathogens. This has resulted in a reduction of the number of effective antibiotics for this disease and begun to pose a major public health threat. Thus, the use of antibiotics is becoming more complicated as resistance increases, necessitating the testing of microbes before treatment, which can sometimes fatally delay the necessary treatment. In addition, wide antibiotic use is further contributing to the problem of resistance. The need to identify new antibiotics is causing the price of these substances to be so high as to be prohibitive in some cases. Therefore, there is a need for new, innovative, and cost-effective approaches to prevent and manage these diseases.

It is believed that the defenses of the Eustachian tube (E tube) and the middle ear (tubotympanum) help to maintain the sterility of the middle ear under normal conditions. To this end, an understanding of the mechanisms that protect the tubotympanum (the middle ear and Eustachian tube) from invading organisms and determine the role that they play in the pathogenesis of OM could prove useful in identifying a new treatment.

SUMMARY OF THE INVENTION

The pharmaceutical composition and a method of treatment of infectious diseases, such as otitis media, paranasal sinusitis, labyrinthitis and meningitis are described. The composition comprises EP2E or homologues thereof.

In one preferred embodiment, a method for the treatment of microbial infections in a mammal is contemplated, which comprises administering to the mammal a pharmaceutical composition that includes at least one component selected from lactoferrins, lysozyme, and defensins in an amount effective for the treatment of such microbial infections. The microbial infections which can be treated by the method of the present invention include otitis media, paranasal sinusitis, labyrinthitis and meningitis. For example, the otitis media, caused by NTHi strain 12, *M. catarrhalis, S. pneumoniae* serotype 3, and *S. pneumoniae* serotype 6B.

In one preferred embodiment, the defensins in the composition of the present invention are alpha-defensins. In yet another preferred embodiment the defensins are beta-defensins, such as beta-defensin 1, beta-defensin 2 and EP2E. Preferably, the EP2E polypeptide is purified from a natural source or is synthesized chemically and refolded by oxidative refolding.

In one preferred embodiment, the pharmaceutical composition of the present invention is administered orally. In another preferred embodiment, the pharmaceutical composition is administered intranasally. In yet another preferred embodiment, the pharmaceutical composition is administered by aerosolization or into the ear canal.

The method and the composition of the present invention can be used in any mammal, including, but not limited to a dog, a cat, a horse, a ferret, a mouse, a rat, a cow, and a primate. Preferably, such primate is human.

BRIEF DESCRIPTION OF THE DRAWINGS

FIG. 11. Multiple sequence a lignment of human beta-defensin proteins from Human Genome Project (Schutte et al. 2002 *PNAS USA* 99:2129-33). DEFB1 (SEQ ID NO: 11); DEFB2 (SEQ ID NO: 12); DEFBP1 (SEQ ID NO: 13); DEFB3 (SEQ ID NO: 14); DEFB4 (SEQ ID NO: 15); DEFB5 (SEQ ID NO: 16); DEFB6 (SEQ ID NO: 17); DEFB7 (SEQ ID NO: 18); DEFB8 (SEQ ID NO: 19); DEFB9 (SEQ ID NO: 20); EP2C (SEQ ID NO: 21); SPAG11(EP2E) (SEQ ID NO: 22); DEFB31 (SEQ ID NO: 23); Consensus (SEQ ID NO: 38).

FIG. 13. Induction of human SPAG11 (EP2E) (SEQ ID NO: 41, GenBank Accession No. AAG21882 from human middle ear epithelial cells HMEEC-1 upon otitis media pathogen challenge.

DETAILED DESCRIPTION OF THE PREFERRED EMBODIMENT

Figure 1:
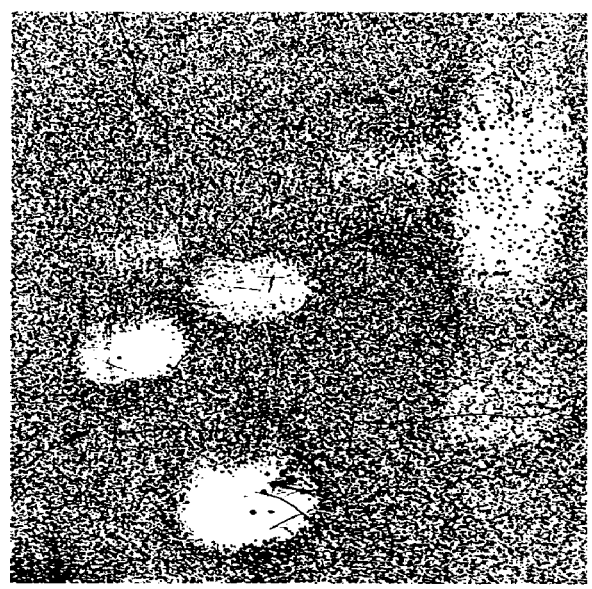
FIG. 1 is a gel overlay assay for the anti-microbial activity of rat middle ear effusion proteins resolved by acid-urea gel electrophoresis. Lane 1, 0.5 mg protegrin; Lane 2, 1 mg human milk lysozyme and human beta-defensin 2; Lane 3, PBS wash of normal middle ear; Lane 4, effusion from middle ear treated with 1.0 mg *S. typhimurium* lipopolysaccharide (LPS).

A method and a composition for the treatment of ear and sinus infections are disclosed. The method and composition take advantage of the fact that some of the body's innate defenses, lysozyme, lactoferrin and the beta-defensins, are typically expressed by middle mucosal ear epithelial cells upon infection. The method and composition also take advantage of the fact that lysozyme and the beta-defensins can cause damage to and inhibit the growth of nontypeable *Haemophilus influenzae* strain 12 (NTHi strain 12), *Moraxella catarrhalis* strain 035E, and *Streptococcus pneumoniae* serotypes 3, and 6B, three bacteria most commonly found to cause otitis media (OM). The studies herein show that the innate immune system may be one of the primary lines of defense against middle ear infections and, thus, future therapies based on these molecules may hold promise for the treatment of otitis media and sinusitis.

Surface epithelia, including the epithelium of the middle ear, form the first barrier against pathogen invasion. Innate immune molecules produced by the epithelial cells provide the host with a constitutive or immediately inducible defense system that is capable of effectively dealing with the continuous attacks of a variety of pathogens at the mucosal epithelial surfaces. Like that of the lung, the epithelium of the nasopharyngeal tract is constantly exposed to a multitude of microorganisms. Although the nasopharynx is connected to the middle ear cavity via the Eustachian tube, giving pathogens potential access to this site, under normal conditions, the middle ear of humans and laboratory animals remains sterile. Furthermore, non-inflamed tubal and middle ear mucosa have been shown to contain relatively few immunocytes. These findings suggest that the components of the innate immune system may be important in protecting the tubotympanum (middle ear and Eustachian tube) and may be playing the role of the first line of defense, prior to the activation of adaptive immunity, against otitis media pathogens.

The pathogenesis of OM is multi-factorial, with risk factors such as upper respiratory viral infection, poor tubal function, delayed development of the immune system, as well as other environmental and genetic factors, play an important role, depending on the age of the infected individual. Available evidence suggests that the mucociliary system, systemic immunity (humoral and cell mediated) and the complement system play important roles in the protection of the tubotympanum. Recent evidence, however, suggests that other biological defense systems—particularly the innate (natural) immune system—may also be playing a role in the protection of the middle ear against OM pathogens. It is now evident that homeostasis of the nasopharyngeal tract, Eustachian tube and the middle ear is maintained in part by anti-microbial proteins and peptides, including lysozyme, lactoferrin, and the defensins.

In addition, there is a need for non-antibiotic treatment of infections in view of the problems associated with decades of antibiotic use and misuse. The incidence of antibiotic resistance is increasing rapidly to the point where some microbes are resistant to all of the present antibiotics known. This requires a careful choice of treatment as well as reducing the speed of treatment, because it may require testing to identify which antibiotic will be effective for treating the specific microbe. In addition, wide antibiotic use is further contributing to the problem of resistance. Thus, the need to identify new antibiotics is causing the price of these substances to be so high as to be prohibitive in some cases.

Thus, one embodiment is a method for the treatment of infection in the middle ear and sinuses by administering one or more antimicrobial peptides to the middle ear and/or sinuses to inhibit the growth of pathogenic microorganisms. This method is based on an antimicrobial mixture for which one or more components are selected from the group consisting of defensins, lysozyme and lactoferrin, particularly the beta defensins.

Because molecules of the innate immune system including lysozyme, lactoferrin, and the defensins form the first line of defense of the tubotympanum and paranasal sinuses during otitis media and paranasal sinusitis, these molecules present an option to be used alone against otitis media and paranasal sinusitis or to be used in combination with other known methods of treatment, such as antibiotics. These innate mediators mount a rapid response against the invading pathogens, before adaptive immune mechanisms are mobilized in vivo. As such, these molecules represent ideal therapeutic candidates to replace antibiotics as the primary treatment modalities for otitis media, sinusitis, and other types of infections.

The present invention uses these innate immune antibiotic molecules to treat infections. This treatment offers a number of advantages. Unlike existing antibiotics, these molecules are unlikely to induce antibiotic resistance. A further advantage is that these molecules, because they are produced by the host, will not induce allergic reactions. Lastly, the method of the present invention is more cost effective then that of antibiotic treatment.

Lysozyme (Lz)

Lysozyme also known as muramidase, is an important component of innate immunity against pathogens at mucosal surfaces. It catalyzes the hydrolysis of 1-4-glycosidic bonds between N-acetylmuraminic acid and N-acetyl-D-glucosamine, which are constituents of the cell walls of most bacteria. Lz has potent antibacterial properties and is thus an important participant in host defense at mucosal surfaces, pleural fluid and in leukocytes. Recent work has shown that inhibition of cationic antimicrobial proteins such as Lz predisposes the airway epithelium to infection. At mucosal surfaces, Lz expression is confined to specialized epithelial cells, including those of the serous glands of the respiratory epithelium and the Paneth's cell of the gastrointestinal epithelium. Lz is also produced by macrophages and cells of the granulocyte lineages.

Chronic middle ear effusions contain high levels of Lz, which is produced by secretory cells of the middle ear mucosal epithelia, as well as by PMNs and macrophages. Hence, chronic middle ear effusions of humans contain high levels of this protein. The fraction of Lz produced by middle ear epithelial cells, has been shown to account for 50% to 80% of the variation of Lz levels seen in middle ear effusions. The presence of Lz in serous cells of the tubal glands and the secretory epithelial cells suggests a role for this molecule in the defense of the middle ear and Eustachian tube against pathogens. The developmental course of Lz secretion in the murine tubotympanum suggests that its maturation follows that of secretory components and that it occurs postnatally.

In the middle ear, lysozyme is produced by the secretory cells of the epithelium, as well as by the PMNs and macrophages. Hence, chronic middle ear effusions of humans contain high levels of this protein. The presence of lysozyme in serous cells of the tubal glands and the secretory epithelial cells suggests a role for this molecule in the defense of the tubotympanum against pathogens.

Lactoferrin (Lf)

Lactoferrin is an iron-binding glycoprotein found in the milk and exocrine secretions of mammals and which is released from neutrophilic granules during inflammation. Lf receptors have been detected on activated T and B cells, monocytes, intestinal brush border cells, platelets and neoplastic cells. Ingested microorganisms are destroyed in cellular phagosomes containing proteolytic enzymes, including Lf. Arnold and colleagues demonstrated a bacterial killing property of Lf on a variety of bacteria. It also has been shown that Lf synergistically interacts with immunoglobulins, complement, and neutrophil cationic proteins against Gram-negative bacteria. Moreover, Lf can damage the outer membrane of Gram-negative bacteria. It has been well established that breast milk fed babies are more resistant to otitis media than babies fed cow milk. Antibacterial lysozyme and Lf in human milk may contribute to the protection of breast fed babies from otitis media.

It was recently shown that, in addition to its iron-binding properties, Lf possessed proteolytic activity. This activity was first discovered when strains of NTHi were cultured in the presence of human milk whey. The only substrates identified for the proteolytic activity of Lf to date are two related proteins of NTHi, the non-pilus Hap adhesin and the IgA protease precursor. Other outer membrane proteins of NTHi, such as P2, P5 and P6 are unaffected. The proteolysis of pilus Hap adhesin and the IgA protease precursor yields several large fragments, suggesting that Lf attacks specific peptide bonds in these proteins. Furthermore, although the proteolytic activity of Lf causes Hap-positive NTHi strains to lose their ability to adhere to Chang epithelial cells and removes most of the IgA protease inhibitor from the outer membrane of these bacteria, it does not affect the viability of the bacteria. The biological importance of the Lf hydrolysis of NTHi is presently unknown, but the effect may be to attenuate the pathogenicity of this microorganism.

Lf belongs to the gene family that includes transferrin (Tf) and the melanoma surface antigen P97, and shows a high level of homology in both its sequence and genomic organization with transferrin. To date, Tfs and Lfs from a variety of sources and cells have been cloned. Pierce and colleagues screened a lactating mammary gland cDNA library with rat liver Tf as probe as well as with a human Lf cDNA in order to pull out the rat Tf and Lf clones. Their results suggest however, that Lf is either not expressed by the rat mammary gland or that it is expressed at undetectably low levels. Previous results suggest that a similar situation may exist in the rat tubotympanum. Previous results herein were not able to demonstrate expression of Lf in rat tubotympanal epithelial cells or in the tissue. Without being restricted to the following theory, it is possible that Lf is absent in rat and Tf may have replaced its function. Lf has also been detected in middle ear effusion, and has been localized to the serous cell of the Eustachian tube glands and to the cuboidal epithelium area (containing the serous cells) of the transition zone of the middle ear. These data suggest that Lf may play a role against bacterial infection of the middle ear and Eustachian tube.

Defensins

Antimicrobial peptides have been identified as key elements in the innate host defense against infection. The defensins are cationic (polar) molecules with antimicrobial activity and have spatially separated hydrophobic and charged regions which have antimicrobial activity. In vitro, defensins (at micromolar concentrations) have a broad spectrum of antimicrobial activity against bacteria, fungi, and even some enveloped viruses. Defensins are considered to be among the earliest developed molecular effectors of innate immunity. They are highly conserved molecules being present in many animal classes (mammals, birds, insects and amphibians). In mammals and birds, defensins are among the most abundant polypeptides secreted by phagocytic white blood cells involved in host defense against bacteria and fingi. During phagocytosis, ingested microbes are exposed to very high concentrations of defensins. The defensins may also have roles in protecting the host, based on their capacity to chemoattract T cells, to promote host immunity, and to activate the classical complement pathway.

Defensins are short peptide molecules with a primary chain length of 29 to 35 amino acids and molecular weight of 3.5 to 4.5 kDa. They are cationic, variably arginine rich and contain six conserved cysteine residues which form three intramolecular disulphide bonds that stabilize a rigid three dimensional K sheet structure. They function as dimers by creating voltage sensitive channels in the plasma membrane of the target organism. The antimicrobial spectrum of defensins encompasses gram positive and gram negative bacteria, fungi and viruses (including HIV & HSV). Defensins may also promote a rapid cellular immune response to infection via a chemotactic effect on monocytes. In addition to their antimicrobial actions defensins may accelerate wound healing, by virtue of their mitogenic effect on epithelial cells and fibroblasts.

Based on the pattern of cysteine connectivity, the mammalian defensins can be divided into two major subgroups termed alpha- and beta-defensins. In alpha-defensins, invariant disulfide bonds are formed in a 1-6, 2-4, and 3-5 order (Selsted, M. E. & Harwig, S. S. 1989 *J Biol Chem* 264: 4003-4007), whereas beta-defensins exhibit a 1-5,2-4, and 3-6 cysteine pairing (Tang, Y. Q. & Selsted, M. E. 1993 *J Biol Chem* 268:6649-6653). Although disulfide linkages differ, the three-dimensional structure of both groups of peptides is very similar including an antiparallel beta-sheet as a major element of secondary structure (Zimmermann, G. R. et al. 1995 *Biochemistry* 34:13663-13671).

In humans alpha-defensins are largely present in neutrophils (alpha-defensins 1-4) and in the small intestinal Paneth cells (alpha-defensins 5 & 6). Beta-defensins have a wider cellular distribution than alpha-defensins, beta-defensin 1 being expressed by the pancreas, kidney and respiratory epithelium. Recently beta-defensin 2 was demonstrated in the skin and bronchial mucosa.

The first mammalian beta-defensin was discovered from the bovine respiratory tract, named tracheal antimicrobial peptide (Diamond, G. et al. 1991 *PNAS USA* 88:3952). Subsequently, lingual antimicrobial peptide was isolated from the bovine tongue (Schonwetter, B. S. et al. 1995 *Science* 267:1645).

Figure 21:
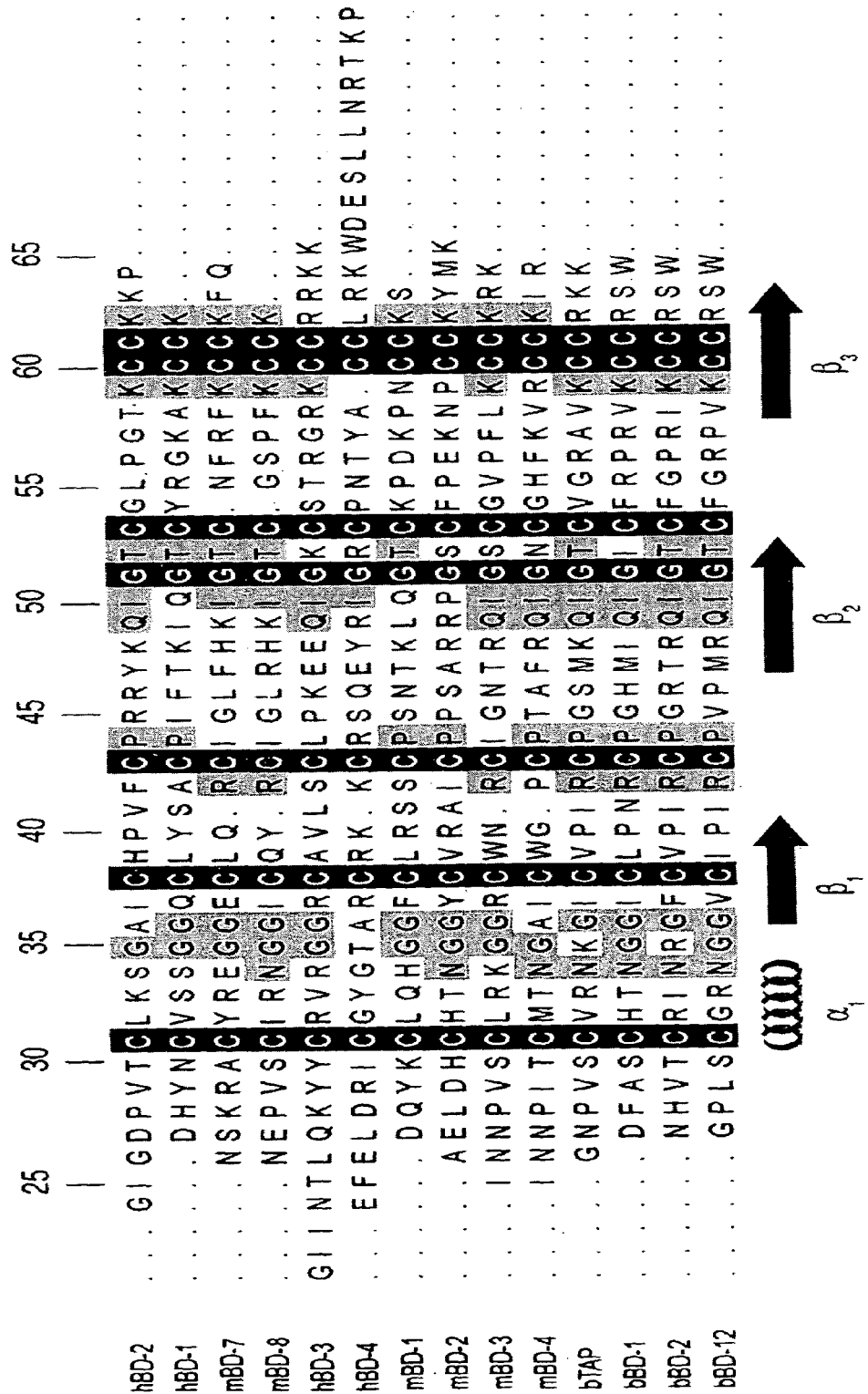
FIG. 21. Sequence alignment of mammalian beta-defensins (BD). The alignment includes the sequences of four human defensins (hBD-1 (SEQ ID NO: 25), hBD-2 (SEQ ID NO: 24), hBD-3 (SEQ ID NO: 28), hBD-4 (SEQ ID NO: 29)), six murine defensins (mBD-1 (SEQ ID NO: 30), (SEQ ID NO: 31), (SEQ ID NO: 32) to mBD-4 (SEQ ID NO: 33), mBD-7 (SEQ ID NO: 26), mBD-8 (SEQ ID NO: 27)), three bovine defensins (bBD-1 (SEQ ID NO: 35), bBD-2 (SEQ ID NO: 36), bBD-12 (SEQ ID NO: 37)), and the bovine tracheal antimicrobial peptide (bTAP (SEQ ID NO: 34)). Strictly conserved amino acid residues are highlighted by a black box and residues occurring with a frequency of 50% are marked by gray boxes. The alignment was generated using the programs ClustalW (Higgins, D. G. et al. 1992 *Comput Appl Biosci* 8:189-191) and Alscript (Barton, G. J. 1993 *Protein Eng* 6:37-40). Because of the low sequence similarity, DALI analysis (Holm, L. & Sander, C. 1996 *Science* 273:595-603) of the three-dimensional structures was used to allow a correct placement of the gaps in the sequences of mBD-7 and mBD-8. Elements of secondary structure found in hBD-1, hBD-2, mBD-7, and mBD-8 are schematically indicated below the alignment. The numbering scheme refers to the full-length hBD-2 including the amino-terminal signal sequence.

The beta-defensins were originally discovered in mammals as antimicrobial peptides of the airway epithelial cells (Selsted, M. E. et al. 1993 *J Biol Chem* 268:6641-6648). Four human beta-defensin (hBD) isoforms have been identified to date: hBD-1, -2, -3, and -4 (Bensch, K. W. et al. 1995 *FEBS Lett* 368:331; Harder, J. et al. 1997 *Nature* 387:861; Harder, J. et al. 2001 *J Biol Chem* 276:5707; Garcia, J. R. et al. 2001 *FASEB J* 15:1819). In humans, an abundant beta-defensin 1 (hBD-1) was initially discovered by analysis of large quantities of hemofiltrate (Bensch, K. W. et al. 1995 *FEBS Lett* 368:331-335). hBD-1 mRNA is constitutively expressed in numerous tissues, including the gingiva, parotid gland, buccal mucosa, and tongue (Mathews, M. et al. 1999 *Infect Immun* 67:2740-2745; Sahasrabudhe, K. S. et al. 2000 *J Dent Res* 79:1669-1674). A second human beta-defensin (hBD-2) is an inducible product of airway epithelia representing the dynamic component of the local epithelial defense system (Schroder, J. M. & Harder, J. 1999 *Int J Biochem Cell Biol* 31:645-651; O'Neil, D. A. et al. 2000 *Infect Immun* 68:5412-5415). A third human beta-defensin, hBD-3, was isolated from skin (Harder, J. et al. 2001 *J Biol Chem* 276:5707-5713). In general, each beta-defensin exhibits a distinct spectrum of antimicrobial activity. Beta-defensins are either constitutively expressed or induced upon stimulation by different inflammatory factors. It was reported that both hBD-1 and hBD-2 bind and activate the chemokine receptor CCR-6, thus linking innate and adaptive immunity (Yang, D. et al. 1999 *Science* 286:525-528). A sequence alignment of mammalian beta-defensins is shown in FIG. 21.

HE21, identified as one major splicing variant of the human EP2 gene, also contains the specific cysteine motif (Osterhoff, C. et al. 1994 *Biol Reprod* 50:516; Hamil, K. G. et al. 2000 *Endocrinology* 141:1245; Frohlich, O. et al. 2001 *Biol Reprod* 64:1072; Jia, H. P. et al. 2001 *Gene* 263:211).

All hBDs show potent antimicrobial activity, especially against Gram-negative bacteria, whereas the function of HE21 had not been confirmed (Harder, J. et al. 1997 *Nature* 387:861; Harder, J. et al. 2001 *J Biol Chem* 276:5707; Garcia, J. R. et al. 2001 *FASEB J* 15:1819; Goldman, M. J. et al. 1997 *Cell* 88:553; Valore, E. V. et al. 1998 *J Clin Invest* 101:1633; Bals, R et al. 1998 *J Clin Invest* 102:874).

In mice, mouse beta-defensin (mBD)-1 (SEQ ID NO: 43, GenBank Accession No. AAB72003), -2 (SEQ ID NO: 44, GenBank Accession No. CAB42815), -3 (SEQ ID NO: 45, GenBank Accession No. AAD29573), -4 (SEQ ID NO: 46, GenBank Accession No. NP_062702, -5 (SEQ ID NO: 47, GenBank Accession No. NP_109659), -6 (SEQ ID NO: 48, GenBank Accession No. NP_473415), -7 (SEQ ID NO: 49, GenBank Accession No. NP_631966, -8 (SEQ ID NO: 50, GenBank Accession No. CAC44635), -9 (SEQ ID NO: 51, GenBank Accession No. NP_631965), -11 (SEQ ID NO: 52, GenBank Accession No. NP_631967, -13 (SEQ ID NO: 53, GenBank Accession No. NP_631969), and -35 (SEQ ID NO: 54, GenBank Accession No. NP_631970) have been identified at the National Center for Biotechnology Information (NCBI) gene bank, although the characteristics of mBD-5, mBD-9, mBD-11, mBD-13, and mBD-35 have not been published (Huttner, K. M. et al. 1997 *FEBS Lett* 413:45; Bals, R et al. 1998 *Infect Immun* 66:1225; Morrison, G. M. et al. 1999 *FEBS Lett* 442:112; Bals, R. et al. 1999 *Infect Immun* 67:3542; Jia, H. P. et al. 2000 *J Biol Chem* 275:33314; Yamaguchi, Y. et al. 2001 *J Biol Chem* 276:315; Bauer, F. et al. 2001 *Protein Sci* 10:2470). mBD-1 and mBD-3 are regarded as mouse homologs of hBD-1 and hBD-2, respectively, and also showed antimicrobial activity (Bals, Ret al. 1998 *Infect Immun* 66:1225; Bals, R. et al. 1999 *Infect Immun* 67:3542).

hBD-1 (SEQ ID NO: 39), hBD-2 (SEQ ID NO: 40), and hBD-3 (SEQ ID NO:55, GenBank Accession No. CAC03097) showed the widespread distribution in various organs like urogenital tissues, skin, respiratory tracts, intestinal tracts, testis, and placenta (Zhao, C et al. 1996 *FEBS Lett* 396:319; Fulton, C. et al. 1997 *Lancet* 350:1750; Jr McCray, P. B. et al. 1997 *Am J Respir Cell Mol Biol* 16:343; O'Neil, D. A. et al. 1999 *J Immunol* 163:6718; Garcia, J. R et al. 2001 *Cell Tissue Res* 306:257). Although the tissue distribution of mBD-5, mBD-7, mBD-8, mBD-9, mBD-11, mBD-13, and mBD-35 have not been evaluated in mice, the other known mBD isoforms also show the expression in multiple tissues, such as kidney, esophagus, tongue, trachea, and skeletal muscle (Huttner, K. M. et al. 1997 *FEBS Lett* 413:45; Bals, R et al. 1998 *Infect Immun* 66:1225; Morrison, G. M. et al. 1999 *FEBS Lett* 442:112; Bals, R. et al. 1999 *Infect Immun* 67:3542; Jia, H. P. et al. 2000 *J Biol Chem* 275:333 14; Yamaguchi, Y. et al. 2001 *J Biol Chem* 276: 315).

A novel antimicrobial peptide Bin1b (SEQ ID NO: 42) was identified in the rat epididymis and its putative amino acid sequence includes the conserved six-cysteine motif (Li, P. et al. 2001 *Science* 291:1783). Bin1b is partially homologous with HE21 and more homologous with the chimpanzee epididymal protein EP2E (SEQ ID NO: 56, GenBank Accession No. AAF87722 in its amino acid sequence (Fröhlich, O. et al. 2000 *J Androl* 21:421). Interestingly, Bin1b showed no expression in the other major organs, such as the lung or kidney.

Subsequently, hBD-4 cDNA was identified and its expression was also almost confined to the testis with much lower expression in the gastric atrium (Garcia, J. R. et al. 2001 *FASEB J* 15:1819). These two isoforms are unique in their confined expression pattern.

The beta-defensins are mainly produced by epithelial cells of the skin, kidneys, and trachea-bronchial lining of nearly all vertebrates. Because beta-defensins are released upon microbial invasion and are located at the host-environment interface, such as mucosal surfaces and skin, they may also function to alert the adaptive immune system of vertebrates. Human beta-defensin 2 (hBD-2), encoded by DEFB4 (formerly DEFB2 in humans) genes (Boniotto, et al. 2003 *Genes Immun* 4:251-257), produced by epithelial cells, exhibits potent antimicrobial activity against Gram-negative bacteria and Candida, but is not as effective against Gram-positive *Staphylococcus aureus*. HBD-2 represents the first human defensin that is produced following stimulation of epithelial cells by contact with microorganisms such as *Pseudomonas aeruginosa* or cytokines such as TNF-alpha and IL-1 beta. Human beta-defensin 2 functions as an NF-kB target gene in the intestinal epithelium and blocking NF-kB activation inhibits the up-regulated expression of hBD-2 in response to IL-1 alpha stimulation or bacterial infection. The HBD-2 gene and protein are locally expressed in keratinocytes associated with inflammatory skin lesions such as psoriasis as well as in the infected lung epithelia of patients with cystic fibrosis.

HBD-1, encoded by DEFB1 gene, is not affected by IL-1 alpha and other proinflammatory stimuli, thus suggesting that unlike the inducible HBD-2 protein, HBD-1 may serve as a defense in the absence of inflammation. The presence of HBD-1 has been reported in the pars tensa and pars flaccida of the tympanic membrane and in the meatal skin. In situ hybridization studies localized the HBD-1 mRNA to the epidermal layer of these tissues. The HBD-1 transcripts were also evident in the sebaceous glands and in hair follicles of the meatal skin. In contrast, HBD-1 mRNA was not detected in the tympanal epithelium of the eardrum.

Human beta-defensin 3 (hBD-3) has recently been isolated from human psoriatic scales (Garcia, J. R. C. et al. 2001 *Cell Tissue Res* 306:257-264; Harder, J. et al. 2001 *J Biol Chem* 276:5707-5713) and is widely expressed in skin, placenta, tongue, and other oral tissues (Dunsche, A. et al. 2002 *Eur J Oral Sci* 109:121-124; Garcia, J. R. C. et al. 2001 *Cell Tissue Res* 306:257-264; Harder, J. et al. 2001 *J Biol Chem* 276:5707-5713; Hong Peng, J. et al. 2001 *Gene* 263:211-218). hBD-3 is active against a number of human pathogens, including multiresistant *Staphylococcus aureus* and vancomycin-resistant *Enterococcus faecium* (Harder, J. et al. 2001 *J Biol Chem* 276:5707-5713).

The beta-defensin family has shown activities against gram-positive and gram-negative bacteria, fungi, and enveloped viruses in vitro (Ganz, T., & R. I. Lehrer 1995 *Pharmacol Ther* 66:191-205; Singh, P. K et al. 1998 *PNAS USA* 95:14961-14966). The activities of HBD-1, -2, and -4 have been reported to be predominantly effective against gram-negative bacteria such as *Escherichia coli* and *Pseudomonas aeruginosa* (Garcia, J. R et al. 2001 *FASEB J* 15:819-1821; Singh, P. K et al. 1998 *PNAS USA* 95:14961-14966), with weak or no activity against gram-positive bacteria such as *Staphylococcus aureus* and *Streptococcus pyogenes* (Garcia, J. R et al. 2001 *FASEB J* 15:819-1821; Harder, J et al. 1997 *Nature* 387:861-862; Schröder, J. M. & J. Harder 1999 *Int J Biochem Cell Biol* 31:645-651). HBD-2 was found to be 10-fold more potent than HBD-1 and exhibited activity against *P. aeruginosa* at physiological concentrations (100 ng/ml) (Singh, P. K et al. 1998 *PNAS USA* 95:14961-14966). HBD-4 seemed to be less effective than HBD-2 against selected gram-positive and gram-negative bacteria and yeasts, with the exception of *P. aeruginosa*, for which HBD-4 displayed a greater antimicrobial activity than the other known defensin peptides (Ganz, T., & R. I. Lehrer 1995 *Pharmacol Ther* 66:191-205). In contrast, HBD-3 has shown broad-spectrum activity against both gram-negative and gram-positive bacteria at concentrations much lower than those for other members of the beta-defensin family (Harder, J et al. 2001 *J Biol Chem* 276: 5707-5713). In addition, its activity appears to be less salt sensitive than those of HBD-1, -2, and -4 (Bals, R et al. 1998 *J Clin Investig* 102:874-880; Ganz, T., & R. I. Lehrer 1995 *Pharmacol Ther* 66:191-205; Goldman, M. J. et al. 1997 *Cell* 88:553-560; Singh, P. K et al. 1998 *PNAS USA* 95:14961-14966). Therefore, HBD-3 is considered the most potent beta-defensin peptide described thus far.

Defensins are normally sequestered in cytoplasmic granules with their primary site of action in phagolysosomes, although some peptide is released into the circulation during the course of infection or inflammation. Developmental regulation of the alpha defensins (cryptidins) has been studied in mice, where it has been shown that cryptidin-6 is the most abundant enteric defensin mRNA in the newborn. Paneth cell mRNAs, including cryptidins-4 and -5, lysozyme, matrilysin, and defensin-related sequences, also were detected in RNA from P1 mouse intestine. Unlike adult mice, where only Paneth cells are immunopositive for cryptidin, cryptidin-containing cells were distributed throughout the newborn intestinal epithelium and not in association with rudimentary crypts. In studies of human newborns, it was found that their neutrophils were not deficient in defensins although they were deficient in bactericidal/permeability-increasing protein (BPI), a 55 kD polypeptide that binds with high affinity to bacterial lipopolysaccharides and kills gram-negative bacteria. The human enteric defensins, on the other hand, are present at sub-adult levels in the developing embryo and it is postulated that levels of enteric defensin expression in the fetus may be characteristic of an immaturity of local defense, which is thought to predispose infants born prematurely to infection from intestinal microorganisms.

In vitro, the defensins (at micromolar concentrations) have a broad spectrum of antimicrobial activity against bacteria, fungi, and even some enveloped viruses. In mammals and birds, defensins are among the most abundant polypeptides secreted by phagocytic leukocytes and epithelial cells involved in host defense. During phagocytosis, ingested microbes are exposed to very high concentrations of defensins. The defensins may also have roles in protecting the host, by their capacity to chemoattract T cells, to promote host immunity, and to activate the classical complement pathway.

Surface epithelia, including the epithelium of the middle ear, form the first barrier against pathogen invasion. Innate immune molecules produced by the epithelial cells provide the host with a constitutive or immediately inducible defense system that is capable of effectively dealing with the continuous attacks of a variety of pathogens at the mucosal epithelial surfaces. Like that of the lung, the epithelium of the nasopharyngeal tract is constantly exposed to a multitude of microorganisms. Although the nasopharynx is connected to the middle ear cavity via the Eustachian tube, giving pathogens potential access to this site, under normal conditions, the middle ear of humans and laboratory animals remains sterile. Furthermore, non-inflamed tubal and middle ear mucosa have been shown to contain relatively few immunocytes. These findings suggest that the components of the innate immune system may be important in protecting the tubotympanum (middle ear and Eustachian tube) and may be playing the role of the first line of defense, prior to the activation of adaptive immunity, against otitis media pathogens.

Active Variants and Homologues

Lactoferrin, lysozyme, and the defensins are well-known molecules which have previously been analyzed in detail. Thus, the regions necessary for activity of these molecules are easily identified. Active variants which possess truncations, single or multiple nucleotide transitions and transversions, and additions may be easily identified and produced with little to no loss of activity. In one embodiment, the active variants which are produced contain at least about 60% of the activity of the non-mutagenized protein, including, but not limited to: 65%, 70%, 75%, 80%, 85%, 90%, 95%, and 99% of the activity.

For example, any mammalian lysozyme may be cloned using methods known to one of skill in the art, for example, by PCR or by isolating or purchasing a full-length cDNA from a library (also see Kikuchi, et al. U.S. Pat. No. 4,945,051, issued Jun. 24, 1987 for a method of producing recombinant human lysozyme—both of which are herein incorporated by reference). Using the information in the literature which identifies regions necessary for lysozyme activity, variants can be produced by deleting, truncating, or mutating regions which are not necessary. For example, Connely, et al. U.S. Pat. No. 6,111,081, issued May 30, 1997 and U.S. Pat. No. 5,571,691, issued Oct. 28, 1993 (both herein incorporated by reference) provide a method for cloning and mutagenizing lactoferrin, without affecting its iron binding activity. A number of variants are disclosed.

The beta-defensins are peptides which are generally between about 38 and 42 amino acids which make up a chain having a net charge of +4 to +10. They are further characterized by their content of half-cysteine residues which are distributed in the peptide chain separated by several intervening residues. The first and second half-cysteins are separated by 6 intervening residues; the second and third half-cysteins are separated by 3 or 4 intervening residues; the third and fourth half-cysteins are separated by 9 intervening residues; the fourth and fifth half-cysteins are separated by 5 or 6 intervening residues; and the fifth and sixth half-cysteins are adjacent. Furthermore, the cysteine residues are paired via disulfide bonds in a characteristic manner: the first cysteine to the fifth cysteine; the second cysteine to the fourth cysteine, and the third cysteine to the sixth cysteine. Some beta-defensins are characterized by a pyroglutamate residue at the amino terminus which makes these molecules resistant to most aminopeptidases. Thus, one of skill in the art, having this detailed information about beta-defensins as well as that in the literature could identify mutations which would have the least affect on the antimicrobial activity (see also Selsted, et al., U.S. Pat. No. 6,211,148, issued Dec. 11, 1997 herein incorporated by reference).

However, in all cases, the antimicrobial activity of the mutants may be tested in a radial assay, such as that detailed in Example 1 or any other assay known to one of skill in the art.

Homologues of these molecules may be identified in all mammals. Thus, homologues may be identified which may be used for the treatment of infections in other mammals, including, but not limited to: dogs, cats, horses, monkeys, apes, cows, sheep, pigs, and a variety of zoo animals. One of skill in the art may identify homologues by searching known public and private databases. It is envisioned that most homologues have already been identified. However, if a homologue has not yet been identified, one of skill in the art may identify a homologue using known techniques.

For example, should one of skill in the art wish to identify the rhinoceros lactoferrin homologue, he or she may produce probes or primers which are specific to conserved regions of the lactoferrin proteins. The skilled artisan may then purchase or produce a rhinoceros cDNA library and, using the probes or primers, isolate the transferrin homologue. Other methods known to one of skill in the art may also be used to isolate and/or identify homologues.

Anti-microbial Composition

The proteins or active variants of the anti-microbial compounds herein may be purified from a natural source, such as, but not limited to, a body fluid, milk, or neutrophils (see Selsted et al. U.S. Pat. No. 6,211,148). Alternatively, they may be expressed recombinantly and purified by any method known to one of skill in the art. The proteins or active variants are said to be "substantially free of natural contaminants" if preparations which contain them are substantially free of materials with which these products are normally and naturally found. Active variants may be produced using methods known to those of skill in the art. However, typically, the genes coding for the proteins are cloned and mutagenesis is performed on the gene which is then expressed and the mutagenized protein isolated. Natural active variants may also be purified from a mammal which naturally produces such variants.

Compositions for use in the methods herein may contain one or more active proteins or variants selected from the group consisting of lysozyme, lactoferrin, alpha-defensins, and beta-defensins. In one embodiment, the composition contains only one of these proteins. In a further embodiment more than one of these proteins is included in the composition, including but not limited to two, three, and four.

In one embodiment, other treatments are included in the composition. The other treatments may be any treatment which may enhance the anti-microbial properties, reduce the side-effects, enhance uptake, and increase the comfort of the patient. For example, it may be possible to include substances which reduce the drying effect on the membranes, or increase healing of the membranes in the area in which it is to be administered.

Vectors Expressing Proteins or Active Variants

It can be envisioned that one method of administering the lysozyme, lactoferrin, alpha defensins, and beta defensins uses expression vectors which express these proteins. The expression vectors may be targeted to the tissue or cell which is infected or which is near the infected cells. The vectors may be any vectors known to one of skill in the art including but not limited to: viral vectors, plasmid vectors, and naked DNA. Expression from these vectors may be constitutive or may be under the control of a specific promoter, such as a eukaryotic promoter, or an inducible promoter.

One advantage of this method is that for those patients who experience chronic otitis or sinusitis, the presence of a vector may allow the effectiveness of the treatment to last for a longer time.

Method of Administration and Dosage

It is envisioned that the antimicrobial mixture can be administered to any type of infection, by injection, topically, or even orally. The method will depend on the type of infection being treated. For the treatment of otitis media and sinusitis, the antimicrobial mixture may be administered to the ear or the sinuses. The administration may be from the outer ear to the middle ear, e.g. to a patient whose ear drum is pierced and a grommet inserted. Alternatively, if the infection is otitis externa, the administration may be using ear drops. If the infection is of the middle ear, the ear drops may contain a substance which allows permeabilization of the antimicrobial molecules across the ear drum. In a further embodiment, the drug may be administered orally or intranasally where the antimicrobial mixture will act as an antimicrobial agent. Alternatively, the antimicrobial mixture may be administered orally, intravenously, intramuscularly, in the tear ducts, or by inhalation.

Substances which may be used to permeabilize the ear drum and allow entry of the antimicrobial molecules may be any substance which increases the permeability of membranes, such as those which are used to permeabilize skin in dermatology. Examples of such substances include, but are not limited to dimethylsulfoxide (DMSO), dimethylacetamide, methyldecyl sulfoxide, cotton seed oil, caster oil derivatives, fatty acid esters, glycerol, vesicles, liposomes, silicone vesicles (see U.S. Pat. No. 5,364,633 herein incorporated by reference), anionic surfactants, preparations such as those in U.S. Pat. No. 5,500,416, herein incorporated by reference.

A composition is said to be "pharmacologically acceptable" if its administration can be tolerated by the recipient patient. Such an agent is said to be administered in a "therapeutically effective amount" if the amount administered is physiologically significant. Alternatively, the amount may be analyzed by the effect. For example if the chosen amount produces a reduction in the number of microbes.

The dosage of the protein components of the antimicrobial mixture to be administered may vary with the method of administration and the severity of the condition to be treated. In general, however, a dosage of from about 0.1 to 100 mg/kg/dose, and more preferably 0.5 to 50 mg/kg/dose of the drug administered 1 to 8 times a day by the intranasal route, or from 1 to 10 drops of a solution or suspension administered from 1 to 10 and preferably 1 to 6 times a day, to each ear. In a further embodiment, from about 0.01 mg/ml to about 100 mg/ml, including, but not limited to 0.1 mg/ml, 1 mg/ml, 2, mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 30 mg/ml, 40 mg/ml, 50 mg/ml, 60 mg/ml, 70 mg/ml, 80 mg/ml, and 90 mg/ml is administered to the ear, sinuses, or upper respiratory tract at least one time per day. Local administration is preferable because it reduces the chances of unwanted side-effects. However, for systemic administration, a dose of from about 0.01 mg/ml to about 1 g/ml may be administered at least one time per day for at least and including one day.

The composition for administration may additionally include additives, excipients, thickeners, and other substances which allow for more effective administration. Examples include oils, emollients, or other substances which increase the effectiveness and comfort of ear drops, nasal sprays, and inhalable compositions. This may also include substances which enhance the smell or taste.

Additional pharmaceutical methods may be employed to control the duration. Controlled release preparations may be achieved through the use of polymers to complex or adsorb the composition. Alternatively, it is possible to entrap the composition into microcapsules, vesicles, or comparable molecules.

The inhibitory effect of salt is not envisioned to be a problem as long as high concentrations of the antimicrobial molecules are administered. However, to minimize the effect, in one embodiment, the pharmaceutical composition is administered in a salt-free vehicle, including but not limited to: water or acidified water. In a further embodiment, the pharmaceutical preparation is administered with a salt chelator. In a further embodiment, the pharmaceutical preparation is protected from salt by administration within liposomes, microcapsule, or any other method known to one of skill in the art.

The expression of lysozyme (LZ), lactoferrin (LF), and the human beta defensins (HBD) was analyzed in the middle ear and tissue in normal and diseased ears in the Examples below. The effect of these substances on OM pathogens morphologically and as antimicrobials was then tested. From these results a method and composition for the treatment of OM and sinusitis was developed. Selected embodiments of this invention are illustrated in the Examples below.

The examples 1-7 below demonstrate that lysozyme, lactoferrin, beta-defensin 1 and beta-defensin 2 are expressed in middle ear mucosa and that are effective against the tested pathogens. The expression of beta-defensin 2, lysozyme and lactoferrin mRNAs were higher in the inflamed tissue, while the levels of beta-defensin 1 showed minimal change. The PCR results for beta-defensins 1 and 2 were confirmed by immunohistochemical analysis. Previous results are consistent with the PCR results, showing that beta-defensin 2 protein was expressed at a higher level in inflamed mucosa, whereas beta-defensin 1 showed no change.

The bacteria used in the following examples were cultured as follows: Stocks of NTHi12 and *M. catarrhalis* 035E (generous gift of Dr. Xin-Xing Gu) were maintained at −80° C. For experiments, the bacteria were plated on chocolate agar and incubated overnight at 37° C. in 5% $CO_2$. A single colony was then picked and transferred to 10 ml of brain heart infusion (BHI, Becton Dickinson, Cockeysville, Md.), supplemented with hemin (10 µg/ml, Sigma, St. Louis, Mo.) and NAD (10 µg/ml, Sigma, St. Louis, Mo.), and allowed to grow overnight. In the morning, 1/10 volume of the overnight culture was transferred to fresh medium and incubated for 3-hours. The subculture was then washed twice with 10 mM sodium phosphate and the O.D. at 620 nm was determined. For the *S. pneumoniae* serotypes 3 and 6B (generous gift of Dr. Xin-Xing Gu), a 50 µl aliquot of the −80° C. stock was thawed on ice, added to 10 ml of Todd-Hewitt broth (THB, Becton Dickinson, Cockeysville, Md.) and cultured overnight. One tenth of the volume of the overnight culture was then transferred to fresh medium and incubated for 3-hours. The subculture was then washed twice with 10 mM sodium phosphate and the O.D. at 620 µm was determined.

EXAMPLE 1

Expression of innate immune molecules: Lysozyme, Lactoferrin, and human beta defensins in the middle ear and the middle ear mucosa normally and in response to pathogens As shown in FIG. 1, a gel overlay assay was performed to show that experimentally induced effusion in rats contained molecules electrophoretically consistent with the molecules of innate immunity and which had anti-microbial activity. Rats were inoculated with 1.0 mg of *S. typhimurium* endotoxin in 100 µl of sterile saline. Animals were sacrificed after 48 hours and the effusion was collected. The microbicidal activity of the samples was then evaluated using the gel over-lay assay. The radial assay method of Lehrer and coworkers was used, with minor modifications (Lehrer et al., 1991 *J Immunol Methods* 137:167-73). The subcultured bacteria ($4 \times 10^6$ CFU/10 ml underlay gel) were mixed with melted underlay gel at 42° C. (0.1× culture broth—BHI for NTHi and *Moraxella* and THB for *S. pneumoniae*-10 mM sodium phosphate, 0.8% low electroendosmosis (EEO)-type agarose) and poured into 8 cm×8 cm square Petri plates. The gel was allowed to solidify in the Petri plates and wells were punched out with a calibrated 200 µl micropipette tip, cut off at the 50 µl mark (approximately 3 mm). The antimicrobial peptides and proteins were dissolved in 0.01% acetic acid and 4 µl was added to each well. The plates were then incubated for 3 hours at 37° C. in the 5% $CO_2$ incubator. They were next overlaid with the overlay gel (0.5× culture broth, 10 mM sodium phosphate, 0.8% low EEO-type agarose) and covered. The plates were then allowed to incubate overnight at 37° C. in a 5% $CO_2$. The diameter of the zones of inhibition produced by each of the antimicrobial molecules against the OM pathogens (NTHi, *M. catarrhalis* and *S. pneumoniae*) was then measured in three separate experiments and the average and standard deviation were calculated. As shown in FIG. 1 lane 4, the areas corresponding to low molecular weight peptides or proteins (consistent with β-defensins) as well as those corresponding to larger proteins (consistent with lysozyme, lactoferrin, SP-A and SP-D) display anti-microbial activity in this assay (FIG. 1).

Next, normal and inflamed human middle ear tissues derived from biopsies, was analyzed by real-time PCR for lysozyme, lactoferrin, beta-defensin 1 and beta-defensin 2. Real-time PCR was performed as follows. Human middle ear mucosa was collected from patients undergoing surgery. Total RNA was isolated by using the TRIzol reagent (Gibco BRL, Rockville, Md.), according to the manufacturer's protocol. cDNA was generated by reverse transcription (RT), using the Superscript II-kit (Gibco BRL, Rockville, Md.), according to the manufacturer's protocol. Real-time PCR was carried out using human lysozyme, lactoferrin, beta-defensin 1, beta-defensin 2 and beta-actin primers. The primer sequences are as follows:

```
human lysozyme (1223-1395) (XM_006858),
                                         (SEQ ID NO:1)
5'- ACT TTT TGT TGG GCA AT -3' (forward), (SEQ ID NO:2)
5'- AGG CTC ATC TGC CTC AG -3' (reverse);

human lactoferrin (947-1282) (AF332168),
                                         (SEQ ID NO:3)
5'- TCT CCG CCA GGC ACA -3' (forward), (SEQ ID NO:4)
5'- GGA GGC CGA GGA GCA -3' (reverse);
```

```
                               -continued
human beta-defensin 1 (68-321) (XM_005297),
                                                    (SEQ ID NO:5)
5'- CGC CAT GAG AAC TTC CTA CCT T -3'  (forward), (SEQ ID NO:6)
5'- AGT TCA TTT CAC TTC TGC GTC ATT T -3'
(reverse);

human beta-defensin 2 (41-336) (XM_005029),
                                                    (SEQ ID NO:7)
5'- GGG TCT TGT ATC TCC TCT TCT CGT T -3'
(forward), (SEQ ID NO:8)
5'- TGC GTA TCT TTG GAG AGG ATA GTT T -3'
(reverse);

human beta-actin (696-964) (BC_002409)
                                                    (SEQ ID NO:9)
5'-GGG GAA ATC GTG GGT GAG AT-3'  (forward), (SEQ ID NO:10)
5'-GCG TAG AGG TCT TTG CGG ATG -3'  (reverse).
```

Figure 2:
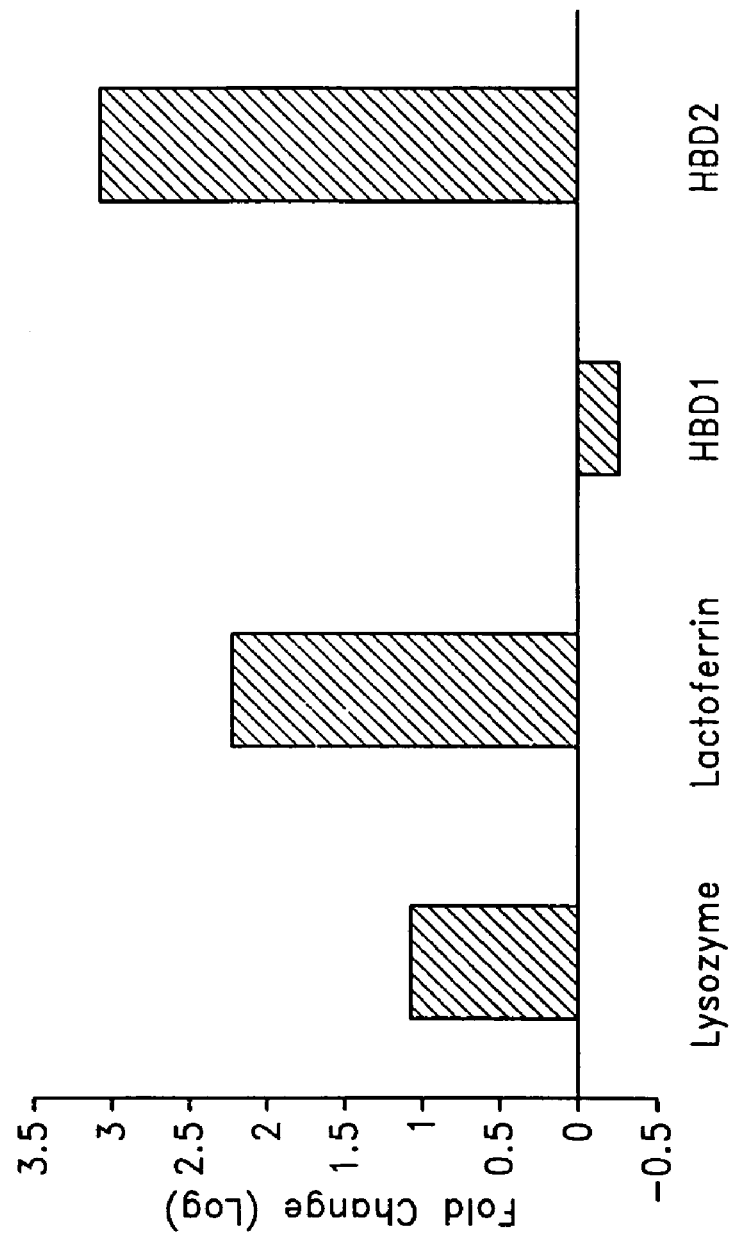
FIG. 2 shows the fold change of mRNA levels for human lysozyme, lactoferrin, beta-defensin 1 (HBD1) (SEQ ID NO: 39, GenBank Accession No. AAC51728) and beta-defensin 2 (HBD2) (SEQ ID NO: 40, GenBank Accession No. AAC69554) from real-time PCR analysis of the expression of these molecules in normal and inflamed middle ear tissue (black bars). The β-actin gene served as the internal standard. RNAs from one sample of normal and one sample of inflamed middle ear tissue were reverse transcribed and subjected real-time PCR. The ordinate is $\log_{10}$ of the fold difference of mRNA levels for each antimicrobial molecule between normal and inflamed middle ear mucosa samples. The results are based on the differences of threshold cycle for each molecule in the normal and inflamed samples.

The PCR mixture contained 200 µM of each primer, 2 µl of template cDNA, and 12.5 µl of SYBR Green master mix (Applied Biosystems, Foster City, Calif.) in a final volume 25 µl of total volume. PCR was carried out in a ABI 7700 Sequence Detection System (Applied Biosystems, Foster City, Calif.) using the following thermal cycling program: 2 minutes at 50° C., 10 minutes at 95° C., followed by 50 cycles of 15 seconds at 95° C. and 1 minute at 60° C. A real-time amplification curve was constructed for each amplification reaction by relating the fluorescence signal intensity (Rn) to the cycle number. The Rn value corresponded to the variation in the reporter fluorescence intensity before and after PCR, normalized to the fluorescence of an internal passive reference present in the buffer solution (6-carboxy-x-rhodamine, a rhodamine derivative). The Ct value (cycle threshold; corresponding to the cycle number at which a significant increase in the fluorescence signal was first detected) was determined for each reaction and served as the basis for comparison of the relative amount of molecule-specific cDNA in each reaction. The Ct for beta-actin was subtracted from the Ct values for each of the other amplified molecules, in order to correct for differences in the amount of starting material. The corrected Ct values for each molecule were compared between the normal and inflamed samples and the cycle difference CD was used to calculate the difference (2CD) for each molecule between the normal and inflamed samples. Human lung cDNA was used as a positive control and for the negative controls, no template was included. PCR products were also analyzed by electrophoresis on a 2% agarose gel containing ethidium bromide in order to ensure that only the specific product was amplified. The results showed that the transcripts for pysozyme, lactoferrin and beta-defensin 2 were present at elevated levels in the inflamed tissues. The beta-actin adjusted threshold cycle differences between normal and inflamed samples for lysozyme, lactoferrin, beta-defensin 1 and beta-defensin 2, were 3.48, 7.38, −0.89 and 10.16, respectively, corresponding to an increase of 11 and 166, and 1150 fold for lysozyme, lactoferrin, and beta-defensin 2 and a decrease of 0.54 fold for beta-defensin 1 (FIG. 2 and Table 1).

TABLE 1

Threshold cycles for human lysozyme (hLz), lactoferrin (hLf), beta-defensin 1 (HBD-1) and beta-defensin 2 (HBD-2), compared between normal and inflamed middle ear mucosa.

| | Average Threshold Cycles | | |
|---|---|---|---|
| | Normal | Inflamed (adjusted to beta-actin) | Normal − Inflamed |
| hLz | 27.37 | 23.89 | 3.48 |
| hLf | 30.83 | 23.45 | 7.38 |
| HBD-1 | 27.91 | 28.80 | −0.89 |
| HBD-2 | 42.46 | 32.30 | 10.16 | cDNAs derived from one sample of normal and one sample of inflamed middle ear tissue were subjected to real-time PCR for the detection of the antimicrobial molecules using SYBER Green I dye on a ABI Prism 7700 Sequence Detection system. The average of three real-time PCR runs is given above for each cDNA. The threshold cycle for beta-actin was 21.94 for normal tissue and 19.72 for inflamed tissue (2.22 cycle difference). In order to control for differences in the amount of starting material, this difference of 2.22 cycles was added to the threshold cycles for the antimicrobial molecules to arrive at the adjusted values.

EXAMPLE 2

The Effect of Lysozyme, Lactoferrin and Human Beta-Defensins on OM Pathogens

The radial assay method of Lehrer and coworkers was used, with minor modifications (Lehrer et al., 1991 *J Immunol Methods* 137:167-73). The subcultured bacteria ($4 \times 10^6$ CFU/10 ml underlay gel) were mixed with melted underlay gel at 42° C. (0.1× culture broth—BHI for NTHi and *Moraxella* and THB for *S. pneumoniae*-10 mM sodium phosphate, 0.8% low electroendosmosis (EEO)-type agarose) and poured into 8 cm×8 cm square Petri plates. The gel was allowed to solidify in the Petri plates and wells were punched out with a calibrated 200 µl micropipette tip, cut off at the 50 µl mark (approximately 3 mm). The antimicrobial peptides and proteins were dissolved in 0.01% acetic acid and 4 µl was added to each well. The plates were then incubated for 3 hours at 37° C. in the 5% $CO_2$ incubator. They were next overlaid with the overlay gel (0.5× culture broth, 10 mM sodium phosphate, 0.8% low EEO-type agarose) and covered. The plates were then allowed to incubate overnight at 37° C. in a 5% $CO_2$. The diameter of the zones of inhibition produced by each of the antimicrobial molecules against the OM pathogens (NTHi, *M. catarrhalis* and *S. pneumoniae*) was then measured in three separate experiments and the average and standard deviation were calculated.

Figure 3:
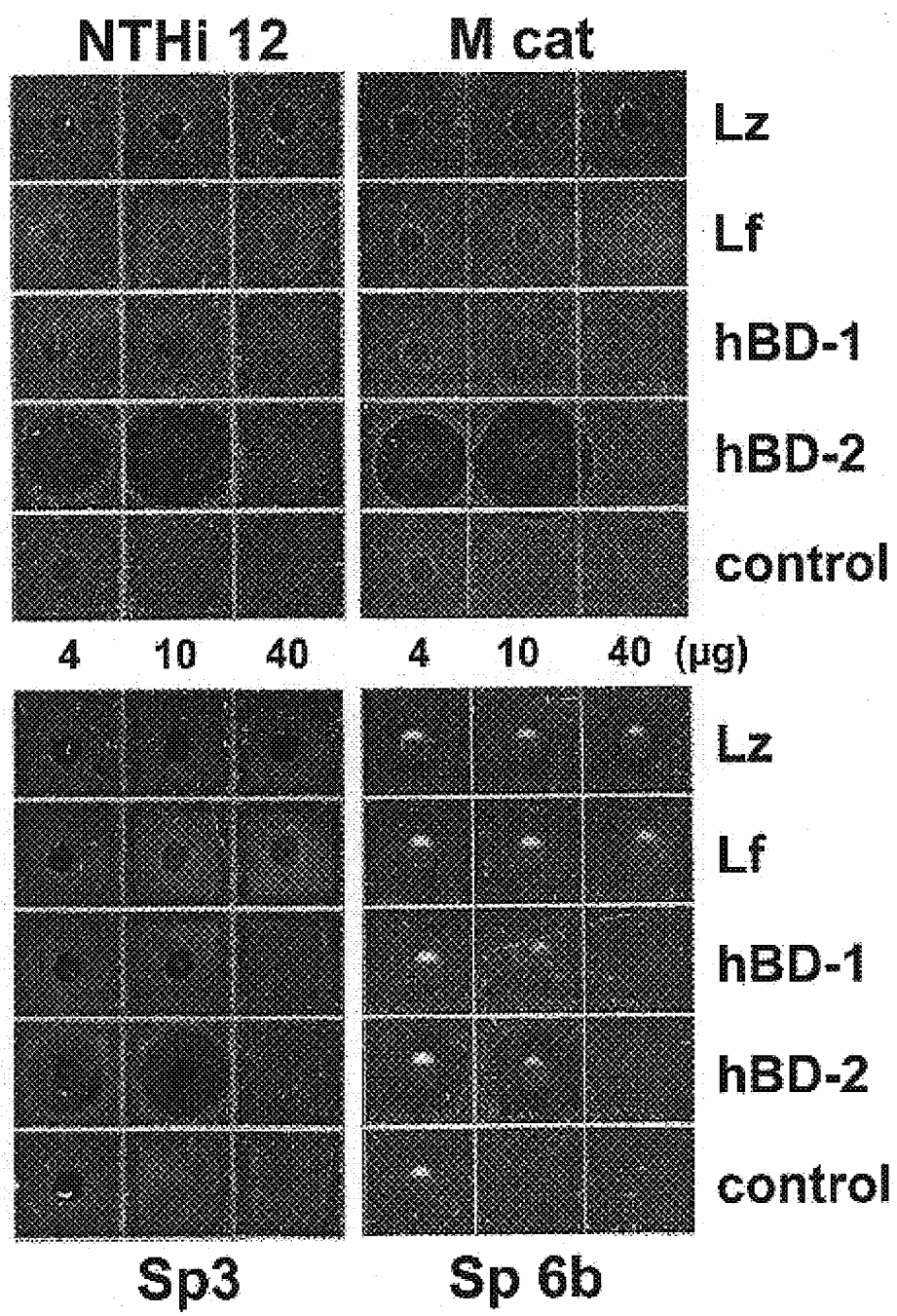
FIG. 3 is a representative radial inhibition assay for the measurement of the activity of innate immune molecules against nontypeable *Haemophilus influenzae* strain 12 (NTHi strain 12), *Moraxella catarrhalis* strain 035E (M. cat), *Streptococcus pneumoniae* serotype 3 (Sp3) and *Streptococcus pneumoniae* serotype 6b (Sp 6b). Three doses (4 μg, 10 μand 40 μg) of human lysozyme (Lz) and lactoferrin (Lf) were tested against the bacteria. For human beta-defensin 1 (hBD-1) and beta-defensin 2 (hBD-2), two doses (4 μg and 10 μg) were tested. Each dose was delivered in a total volume of 4 μl. The control well received only solvent (0.01% acetic acid). The diameter of the inhibition zone was measured and averaged in three separate experiments.

After confirming the expression of the innate immune molecules in the middle ear mucosa, the bacteriostatic/bactericidal effects of these molecules on four OM pathogens, NTHi strain12, *M. catarrhalis* strain 035E, *S. pneumoniae* serotype 3, and *S. pneumoniae* serotype 6B was determined. Treatment of the bacteria with lysozyme resulted in a slight but visible inhibition of the growth of *M. catarrhalis* and *S. pneumoniae* serotype 6B (FIG. 3 and Tables 2 and 3). This effect was seen with 40 µg of peptide per well, equivalent to a concentration of 10 mg/ml. Lysozyme, however, had no effect on NTHi and appeared to enhance the growth of *S. pneumoniae* serotype 3 (FIG. 3 and Table 2). Treatment with beta-defensin 1 was effective only against *M. catarrhalis* and only at the high dose (10 μg—equivalent to 2.5 mg/ml). In contrast beta-defensin 2, at both concentrations (4 and 10 μg—equivalent to 1 and 2.5 mg/ml respectively), significantly inhibited the growth of all four bacterial types (FIG. 3 and Tables 2 and 3). *M. catarrhalis* strain 035E was most susceptible to β-defensin 2, followed by NTHi strain12, *S. pneumoniae* serotype 3 and *S. pneumoniae* serotype 6B. Lactoferrin treatment, conversely, not only did not inhibit bacterial growth, but appeared to result in an enhancement of the growth of *S. pneumoniae* serotype 3 (10 μg—equivalent to 2.5 mg/ml), and *S. pneumoniae* serotype 6B (10 and 40 μg—equivalent to 2.5 and 10 mg/ml respectively) (FIG. 3 and Tables 2 and 3).

of colonies. Interestingly, incubation of the bacteria with a combination of lysozyme and the β-defensins, with or without lactoferrin (1 mg /ml), did not result in a further decrease in the number of viable bacteria. Although these results are slightly different from those produced by the radial assay, without being restricted to the following theory, this may be due to the assay conditions or to the concentration tested. For example, the bacteria may be more sensitive to the antimicrobials in a liquid assay, such as the colony forming assay.

EXAMPLE 3

Dose Response Analysis

A dose response analysis is performed for each molecule in order to determine the concentration range where the best effect is observable as well as a synergistic effect of different combinations. Thus, various concentrations of lactoferrin

TABLE 2

Measurements of the effect of human lysozyme (hLz), lactoferrin (hLf), beta-defensin 1 (HBD-1) and beta-defensin 2 (HBD-2) on the growth of OM pathogens using the radial inhibition assay.

| Molecule | Total amount of protein/peptide added (in a total volume of 4 μl) | Bacteria | | | |
|---|---|---|---|---|---|
| | | NTHi | *M. catarrhalis* | *S. pneumoniae* 3 | *S. pneumoniae* 6B |
| hLz | 4 μg | — | — | — | — |
| | 10 μg | — | — | — | — |
| | 40 μg | — | 4 ± 1.7 (P) | — | 5 ± 1.7 (P) |
| hLf | 4 μg | — | — | — | — |
| | 10 μg | E | — | E | — |
| | 40 μg | E | E | E | E |
| HBD-1 | 4 μg | — | — | — | — |
| | 10 μg | — | 7.7 ± 0.6 (P) | — | — |
| | 40 μg | ND | ND | ND | ND |
| HBD-2 | 4 μg | 9.7 ± 2.5 (C) | 11.7 ± 0.6 (C) | 8.7 ± 1.5 (C) | 8.7 ± 1.2 (C) |
| | 10 μg | 12.3 ± 2.9 (C) | 14.7 ± 0.6 (C) | 10 ± 1.3 (C) | 10.7 ± 1.5 (C) |
| | 40 μg | ND | ND | ND | ND |

Diameter (mm) of the inhibition zone (average of 3 separate experiments+SD) caused by the different concentrations of the antimicrobial molecules is given in the column below each pathogen. –: No effect; E: Enhanced growth; C: Complete inhibition; P: Partial inhibition; ND: Not done.

Figure 4:
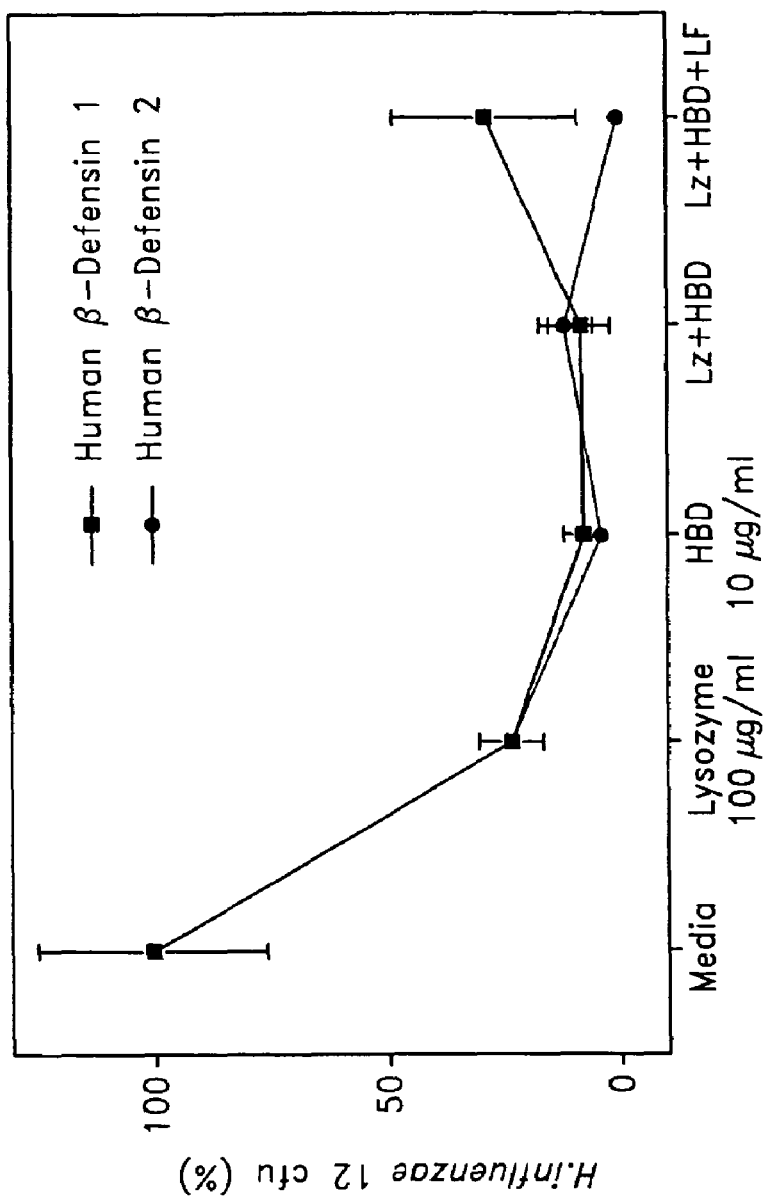
FIG. 4 is a graph demonstrating the inhibition of NTHi growth by beta-defensins 1 and 2, lysozyme and lactoferrin in a colony formation assay.

The ability of a few of these innate immune mediators: human milk lysozyme (Lz), human beta-defensins (HBD) 1 and 2 and human milk lactoferrin (LF) to inhibit the growth of non-typeable *Haemophilus influenzae* (NTHi) at other concentrations was also investigated using a different type of assay, a colony formation assay. The molecules were tested separately, as well as in combination, and the effect on NTHi growth was determined using a colony formation assay. Incubation of cultures of NTHi with 100 μg/ml human milk lysozyme for 3 hours, resulted in an 80% reduction of the number of viable bacteria (FIG. 4). In previous studies, it was shown that the concentration of lysozyme in middle ear effusion can be as high as 3.7 mg/ml and thus the concentrations used in these studies are well within the physiological range. Incubating the bacteria with 10 μg/ml of either human beta-defensin 1 or 2 produced an even more pronounced effect, with close to a 95% reduction in the number with various concentrations of defensins are used as in Example 1 and the concentrations at which maximum effectiveness of the combination occurs are used in further treatments.

EXAMPLE 4

Effect of NaCl

Physiologically, salt concentrations vary depending on the site. However, typically they can be as high as 150 mM. Thus, the salt sensitivity of the antimicrobial molecules was tested. NaCl was added to the gel in Example 2 to obtain a final concentration of 100 mM. As shown in Table 3, 100 mM salt completely blocked the growth inhibitory effect of lysozyme, lactoferrin and beta-defensin 1 against all bacteria tested. It also blocked the effect of β-defensin 2 against *S. pneumoniae* serotype 3 and *S. pneumoniae* serotype 6B. High salt concentration, however did not inhibit the activity of β-defensin 2 against NTHi and *M. catarrhalis*, although it did result in a reduction of this effect.

TABLE 3

Measurements of the effect of 100 mM NaCl on the inhibition of the growth of OM pathogens by human lysozyme (hLz), lactoferrin (hLf), beta-defensin 1 (HBD-1) and beta-defensin 2 (HBD-2), using the radial inhibition assay.

| Molecule | Total amount of protein/peptide added (in a total volume of 4 μl) | Bacteria | | | |
|---|---|---|---|---|---|
| | | NTHi | M. catarrhalis | S. pneumoniae 3 | S. pneumoniae 6B |
| hLz | 4 μg | — | — | — | — |
| | 10 μg | — | — | — | — |
| | 40 μg | — | — | — | — |
| hLf | 4 μg | — | — | — | — |
| | 10 μg | — | — | — | — |
| | 40 μg | — | — | — | — |
| HBD-1 | 4 μg | — | — | — | — |
| | 10 μg | — | — | — | — |
| | 40 μg | ND | ND | ND | ND |
| HBD-2 | 4 μg | 8.8 ± 1.0 (C) | 9.0 ± 0.7 (C) | — | — |
| | 10 μg | 11.3 ± 0.3 (C) | 11.0 ± 0.7 (C) | — | — |
| | 40 μg | ND | ND | ND | ND |

Diameter (mm) of the inhibition zone (average of 3 separate experiments±SD) caused by the different concentrations of the antimicrobial molecules is given in the column below each pathogen. –: No effect; ND: Not done

EXAMPLE 5

Morphological Changes in Response to the Action of Lactoferrin, Lysozyme, and the Human Defensins Molecules of innate immunity can damage the cell wall and membranes of the OM microbes. Thus, in order to determine what the effect of these molecules was, electron microscopy was performed as follows:

Electron microscopy was performed by treating the bacterial cultures with antimicrobial protein or peptide for 3 hours, mixing with an equal volume of 5% buffered glutaraldehyde (pH 7.4) and centrifuging (5000×g, for 20 minutes). The bacterial pellets were left in the fixative at 4° C. for 2 hr, post-fixed in 2% osmium tetroxide, dehydrated in ethanol and embedded in Eponate 12 (Ted Pella, Redding, Calif.). Sections were mounted in coated specimen grids, contrasted with uranyl acetate and lead citrate and examined in a transmission electron microscope (CM120 BioTwin, FEI-Philips, Hillsboro, Oreg.) operating at 80 kV. Images were recorded on photographic film and were subsequently digitized.

Figure 5:
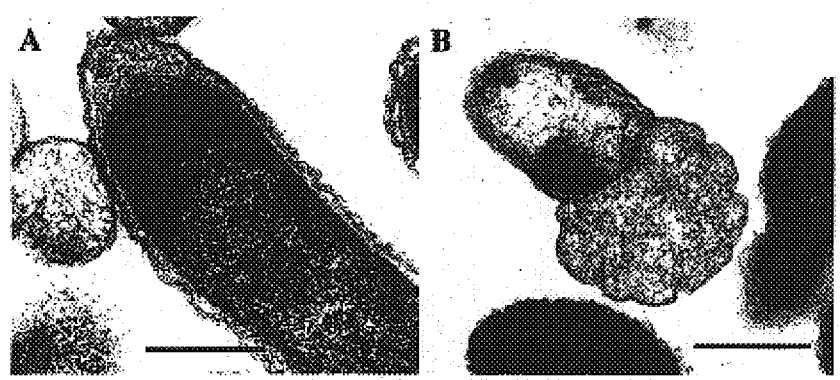
FIG. 5 shows the effect on the ultrastructure of NHTi after treatment with natural antibacterial agents. A) No treatment showing normal appearance of NTHi. An inner membrane encloses the nucleic acid compartment. The outer surface membrane encloses a compartment filled with amorphous appearing material. Bar=100 nm. B) Treatment with lysozyme (100 μg/ml). Few completely lysed bacteria were observed. Bar=0.5 micron.

In order to determine if inhibition of NTHi growth was due to disruption of the bacterial cell wall and membranes, ultrastructural analysis was performed. As shown in FIG. 5 (3 hour), incubation of NTHi with lysozyme 100 μg/ml human milk lysozyme caused sufficient damage to the bacterial membranes that extrusion of the outer membrane could clearly be seen. Morphological changes were also apparent in bacteria treated for 3 hours with 10 μg/ml human beta-defensins 1 and 2, or a combination of lysozyme (100 μg/ml), human milk lactoferrin (1 mg/ml). Thus these immune mediators function very well as antibiotics in the above studies.

Figure 6:
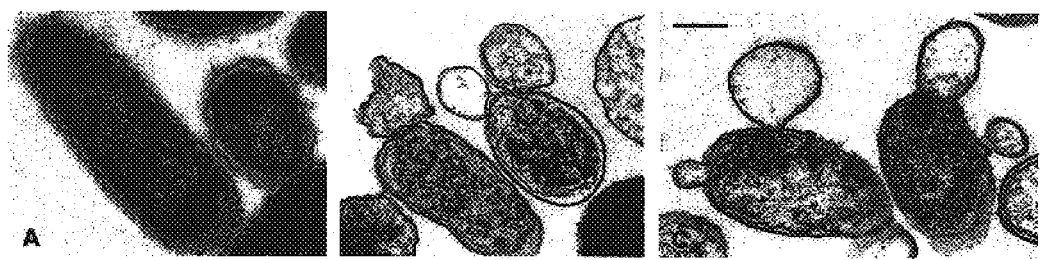
FIG. 6 is an ultra-structural analysis of the effect of human beta-defensin 2 and lysozyme on NTHi showing the damage caused to the bacteria by the treatment. Untreated NTHi are shown in panel A. The bacteria were treated for three hours with β-defensin 2 (10 μg/ml) (panel B), or with 1 mg/ml human milk lysozyme (panel C). Bar=0.2 micron.

Ultrastructural changes were analyzed in NTHi after treatment with lysozyme and beta-defensin 2 (SEQ ID NO: 40). Ultrastructural analysis of NTHi, S. pneumoniae serotype 3, S. pneumoniae serotype 6B and M. catarrhalis treated with the antimicrobial molecules revealed that significant changes occurred in the bacteria following exposure to beta-defensin 2 and lysozyme. The morphology of the untreated NTHi is shown in FIG. 6A. FIGS. 6B and 6C show the morphology of NTHi treated with 10 μg/ml beta-defensin 2 for 3 hours, and 1 mg/ml of human milk lysozyme for 3 hour, respectively. The results showed that in the presence of β-defensin 2 and lysozyme, NTHi show blebbing of the membranes with extrusion of the cytoplasmic contents into the blebs (FIGS. 6B and 6C). Moreover, none of the untreated bacteria showed any evidence of blebbing suggesting that the observed changes were not fixation artifacts. From examination of over 100 EM fields, it can be envisioned that with either of the antimicrobial molecules, at least 30% of the bacteria showed signs of membrane damage. At the time points measured, there did not appear to be any ruptured NTHi. A one hour treatment of the bacteria with β-defensin 2 also showed similar results, suggesting that the effect on the bacteria was occurring relatively quickly. Furthermore, the morphology and the proportion of affected to non affected cells were similar in NTHi treated with lysozyme for the one hour, as compared to those treated with this molecule for 3 hours.

Figure 7:
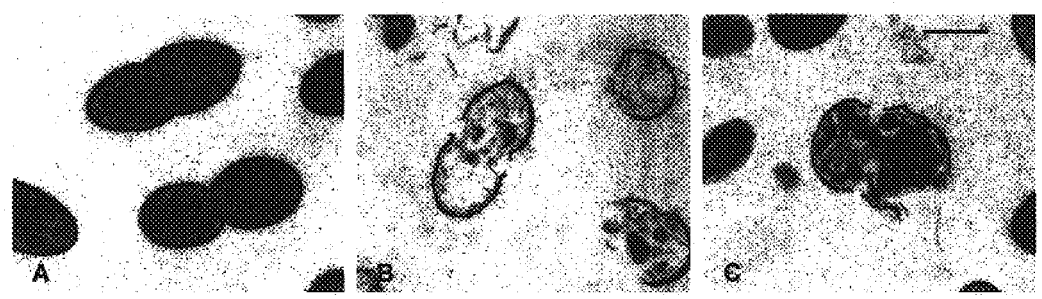
FIG. 7 is an ultra-structural analysis of the effect of human beta-defensin 2 and lysozyme on *S. pneumoniae* serotype 3 showing the damage caused to the bacteria by the treatment. Untreated bacteria are shown in panel A. The bacteria were treated for three hours with human beta-defensin 2 (10 μg/ml) (panel B), or with 1 mg/ml human milk lysozyme (panel C). Untreated NTHi are shown in panel B. Bar=0.5 micron.

Treatment of S. pneumoniae serotype 3 with beta-defensin 2 and lysozyme also resulted in damage to the bacteria, although the former molecule appears to be much more potent. The untreated bacteria are shown in FIG. 7A, while FIGS. 7B and 7C show the effect of a three-hour treatment with beta-defensin 2 and lysozyme, respectively. As seen in FIG. 7B, treatment with beta-defensin 2 results in disappearance of the capsule in certain regions and the lysis of the bacteria. Although lysozyme has a similar effect, many fewer bacteria appear to be lysed, consistent with the results of the radial assay.

Figure 8:
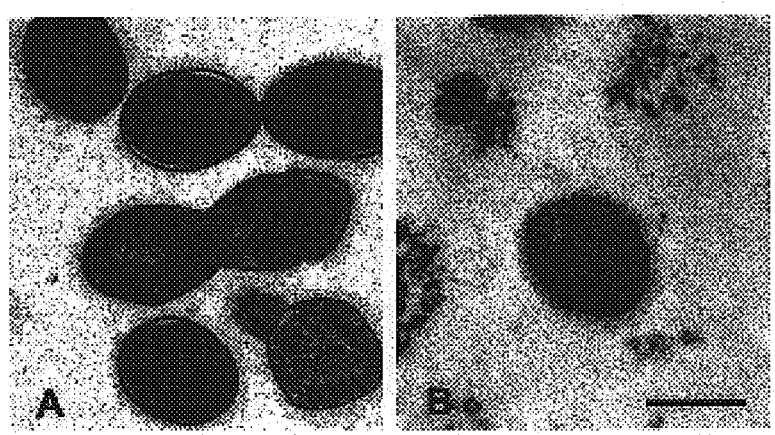
FIG. 8 is an ultra-structural analysis of the effect of human beta-defensin 2 on *S. pneumoniae* serotype 6B showing the damage caused to the bacteria by the treatment. Untreated bacteria are shown in panel A. The bacteria were treated for three hours with human beta-defensin 2 (10 μg/ml) are shown in panel B. Bar=0.5 micron.

Human β-defensin 2 showed activity against S. pneumoniae serotype 9B as well. As shown in FIG. 8A, these bacteria are capsulated with a distinct cell wall. A three-hour treatment with beta-defensin 2, however resulted in damage to the capsule and condensation of the cytoplasmic material (FIG. 8B). The effect of lysozyme was not tested on this bacterium.

Figure 9:
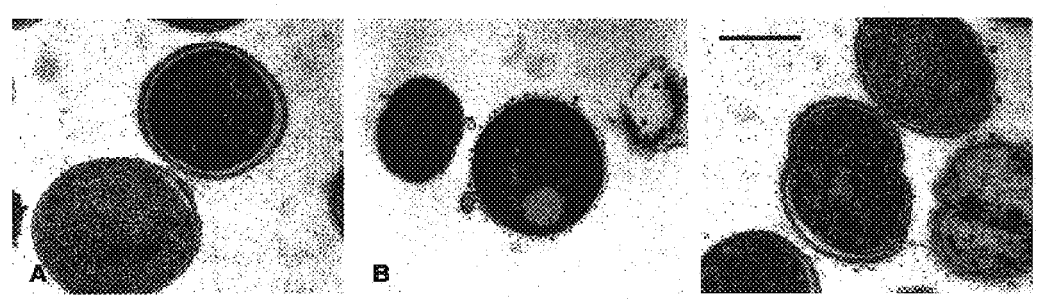
FIG. 9 is an ultra-structural analysis of the effect beta-defensin 2 and lysozyme on *M. catarrhalis*. Untreated bacteria are shown in panel A. Results of a 1-minute treatment of the bacteria with lysozyme are shown in panel B and those of a 30-minute incubation with beta-defensin 2 are shown in panel C. Bar=0.5 micron.

The effect of β-defensin 2 and lysozyme on M. catarrhalis was also tested. As shown in FIG. 9A, untreated M. catarrhalis have a distinct lobulated capsule. Results of a 1-minute treatment of the bacteria with lysozyme are shown in FIG. 9B and suggest that this treatment can result in the formation of blebs. Samples from later time points, however, showed no evidence of blebs and, as expected, contained more lysed bacteria. As shown in FIG. 9C, a 30-minute incubation of *M. catarrhalis* with beta-defensin 2 resulted in substantial damage to the cells.

Of the four molecules tested in the radial inhibition assay, beta-defensin 2 displayed the highest potency and was effective against all four pathogens tested. NTHi and *M. catarrhalis* are both Gram negative bacteria and the effect of beta-defensin 2 on their viability is consistent with other studies. None of the treated NTHi showed any evidence of the presence of mesosome-like structures such as those seen in *S. aureus* treated with defensins. It is interesting, however, that treatment of the NTHi with lysozyme, although effective at the ultrastructural level, had no effect on the viability of the bacteria. Similar results were obtained by Shimoda and coworkers, when they exposed *S. aureus* to defensins (Shimoda et al., 1995 Infect Immun 63:2886-91). The effect of beta-defensin 2 on the viability of a Gram positive bacteria, *S. pneumoniae*, however, was unexpected and is an unexpected finding.

The observed activity of beta-defensin 1 (SEQ ID NO: 39) against *M. catarrhalis* is also consistent with previous observations of the antimicrobial activities of this molecule against Gram negative bacteria. None of the other pathogens, including NTHi, were affected by beta-defensin 1 treatment suggesting that this defensin molecule is less active than β-defensin 2 against OM pathogens. As expected, both molecules showed salt sensitivity and were inhibited by 100 mM salt Lysozyme caused no detectable inhibition in the growth of *S. pneumoniae* serotype 3 and NTHi, while it showed only minimal activity against *M. catarrhalis* and *S. pneumoniae* serotype 6b. Lysozyme is a muramidase that cleaves the glycan backbone by catalyzing the hydrolysis of 1-4-glycosidic bonds between N-acetylmuraminic acid and N-acetyl-D-glucosamine, which are constituents of the cell walls of most bacteria. Studies of the cell wall of *S. pneumoniae*, however, have shown that a very high proportion of the hexosamine units (greater than 80% of the glucosamine and 10% of the muramic acid residues) are not N-acetylated, thus rendering the peptidoglycan of these bacteria to be resistant to the hydrolytic action of lysozyme. It is of interest that the growth of and *S. pneumoniae* serotype 6b is slightly inhibited by lysozyme, while that of *S. pneumoniae* serotype 3 is unaffected. The results suggest that even minor changes in the cell wall of bacteria, such as those that may exist between the different serotypes of *S. pneumoniae*, may have a profound effect on the resistance of the bacteria to this innate immune molecule. Consistent with previous observations, lysozyme also displayed salt sensitivity and its effect was inhibited by 100 mM salt.

Lactoferrin is an iron-sequestering glycoprotein that predominates in mucosal secretions. The presence of molecules such as lactoferrin allows free extracellular iron to be kept at levels ($10^{-18}$ M) that do not allow bacterial growth and thus represents a mechanism of resistance to bacterial infections by prevention of colonization of the host by pathogens. Although this function of lactoferrin plays an important role in the protection of mucosal surfaces, bacteria have evolved mechanisms that allow them to use lactoferrin's iron-sequestering to their benefit. Thus, unlike the results obtained with lysozyme and the β-defensins, treatment of the four OM pathogens with lactoferrin appeared to have a growth enhancing effect. All four bacteria tested had a positive growth response to lactoferrin, with NTHi strain 12 and *S. pneumoniae* serotype 3 showing a higher sensitivity than the other two. This result is, however, not surprising, as *M. catarrhalis* has been shown to be able to use lactoferrin as an iron source for growth in vitro and *Streptococcus pneumoniae* has been shown to specifically recognize and bind human lactoferrin. Moreover, other bacteria have also been shown to be able to use lactoferrin for growth. When grown under iron starvation, *Neisseria meningitidis* expresses receptors for transferrin and lactoferrin in the outer membrane. Iron transport mutants of *Helicobacter pylori* have also been shown to be able grow in the presence of lactoferrin and transferrin. Lactoferrin saturated with iron has been shown to enhance the intracellular growth of *Legionella pneumophila* in HeLa cells. However, it is possible that the effect of lactoferrin in enhancing the growth of these microbes may be restricted to the in vitro environment and when administered in vivo, lactoferrin may exhibit an inhibitory role. In addition, not all bacteria have evolved methods to use lactoferrin, thus, lactoferrin may be more useful against bacteria other than those currently found most commonly in OM. It is envisioned that the bacteria found most commonly in OM may change in the future with other bacteria becoming more predominant as causative agents of OM. Thus, antimicrobials such as lactoferrin may become more useful.

The results of the electron microscope studies suggest that beta-defensin 2 and lysozyme have a profound effect on structural integrity of NTHi, *S. pneumoniae* serotype 3, *S. pneumoniae* serotype 6B and *M. catarrhalis*. Beta-defensin 2 is a cationic peptide known to damage bacterial outer membranes, while lysozyme is known to disrupt the bacterial cell wall. These findings appear to be consistent with earlier observations of the effect of these molecules on bacterial integrity.

The following U.S. patents contain related subject matter and are herein incorporated by reference: U.S. Pat. Nos. 5,242,902; 4,268,519; 5,240,909; 5,834,424; 4,961,927; 5,962,410; and 5,910,479.

Thus, in one embodiment of the invention, the pharmaceutical preparation herein comprises β-defensin 2. In a further embodiment, the pharmaceutical preparation herein comprises beta-defensin 2 and lysozyme. In a further embodiment, the pharmaceutical preparation herein comprises beta-defensin 2, lysozyme, and beta-defensin 1. It is envisioned that for the treatment of some microbes, lactoferrin is not used due to the fact that these microbes have developed ways of using lactoferrin. In a further embodiment, a pharmaceutical preparation of beta-defensin 2, lysozyme, and beta-defensin 1 is used to treat an OM infection caused by *M. catarrhalis*. In a further embodiment, a pharmaceutical preparation comprising beta-defensin 2, and lysozyme is used to treat OM caused by *S. Pneumonia* serotype 6B. In a further embodiment, a pharmaceutical preparation of β-defensin 2, lysozyme, and beta-defensin 1 is used to treat an OM infection caused by NTHi strain 12. In a further embodiment, a pharmaceutical preparation of beta-defensin 2 is used to treat an OM infection caused by *M. catarrhalis*. However, it is envisioned that a pharmaceutical preparation comprising beta-defensin 2, lysozyme, and beta-defensin 1 at different concentrations may be useful for the treatment of any OM infection.

EXAMPLE 6

Figure 10:
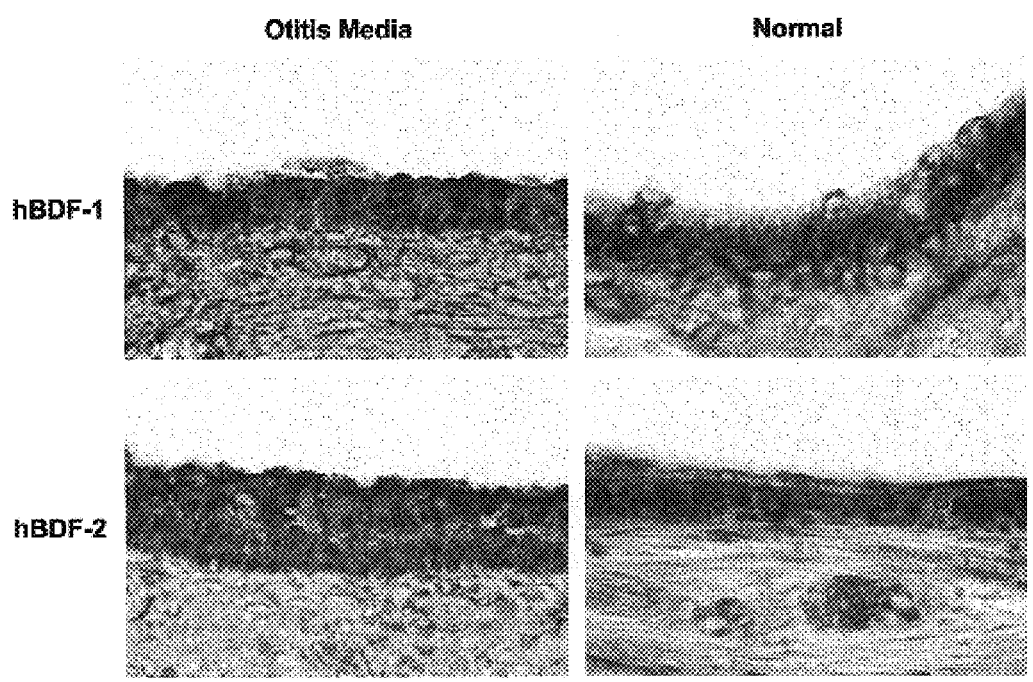
FIG. 10 shows immunolabeling of archival temporal bone sections showing no change in beta-defensin 1 expression between otitis media (OM) and control. However, human beta-defensin 2 is expressed at high levels in middle ear epithelium from OM patients, but not in normal subjects.

Expression of Changes in Response to the Action of Lactoferrin, Lysozyme, and the Human Defensins Immunohistochemistry was performed using Celloidin embedded 20 µM thick sections of normal and inflamed mucosa, from archival temporal bone specimens were obtained from the House Ear Institute's Temporal Bone Collection. Following de-celloidination with ether and absolute ethanol, non-specific binding sites on the slides were blocked using normal goat serum. The sections were then subjected to antigen retrieval (Vector Laboratories, Burlingame, Calif.) and incubated with polyclonal antibodies against human β-defensin 2—1:500 dilution. Signals were detected by the avidin/biotin complex (ABC) method (Vector Laboratories). As shown in FIG. 10 A and B (lower panel) beta-defensin 2 was expressed in tissue from the diseased, but not the normal middle ear. These results are consistent with studies of human beta-defensin 2 that have shown this molecule to be highly inducible by inflammatory stimuli, with minimal expression in non-challenged tissue or cells. The expression of beta-defensin 1 was also examined in these sample, but, as expected, there was little to no difference in levels of this molecule in normal versus diseased epithelium (FIG. 10 A and B, upper panel).

EXAMPLE 7

Treatment of an OM Infection Caused by *M. Catarrhalis*

A pharmaceutical preparation comprising Lysozyme, beta-defensin 1, and beta-defensin 2 at a concentration of 10 mg/ml Lysozyme, 10 mg/ml beta-defensin 1, and 1 mg/ml beta-defensin 2 is produced for administration to the middle ear of a patient whose ear drum is pierced. A grommet is inserted into the outer ear up to the middle ear and the pharmaceutical preparation is applied. Application is repeated 2× per day for 2 weeks. If the infection returns, the treatment is repeated.

EXAMPLE 8

Human SPAG11 (EP2E) and its Rat Homolog Bin1b are Inducible Beta-Defensin Peptides with Limited Tissue Expression and Antimicrobial Activity in Tubotympanum Beta-defensins are cationic peptides produced by epithelial cells that have been proposed to be an important component of immune function at mucosal surfaces. Similarities between mammalian beta-defensins may permit the use of rat models to further define the role of these peptides in innate host defense. Rat Bin1b (Li P. Et al. 2001 *Science* 291:1783-5) is a peptide that exhibits homology at the gene level to human SPAG11 (EP2E), which has homology with beta-defensin family identified in man (FIG. 11). We hypothesized that: 1) Middle ear cavity is protected by a highly effective innate immune system consisting of epithelial cell derived bactericidal molecules as well as complement and phagocytes; and 2) Members of beta-defensins family are expressed by the tubotympanal epithelial cells and are among nature's most potent antimicrobials. Upon these hypotheses, the purpose of this study was to determine the antimicrobial activity of Bin1b, the tissue distribution of Bin1b expression in the ear, and the effect of bacterial infection on Bin1b expression.

Materials and Methods

Q-PCR. Bin1b mRNA expression was assayed by Quantitative polymerase chain reaction (Q-PCR) using cDNA derived from each organ of the ear. Expression of Bin1b was also evaluated in tissues obtained from rat 4 h after injection to middle ear cavity, which had been sensitized 24 hours before with LPS using Q-PCR.

Peptides, refolding and Antimicrobial Assays. Based on the sequence deduced from Bin1b cDNA, a 43-amino acid peptide was assembled using automated [n-(9-fluorenyl) methoxycarbonyl] solid-phase synthesis. Bin1b and SPAG 11 (EP2E), each of which was homogeneous by electrophoretic and mass spectrum analysis, were quantified by UV absorbance at 280 mm they were tested for antimicrobial activity against bacterial strains (*E. coli* ML35p, *M. catarrhalis*, NTHi, and *S. pneumoniae* T3) in a CFU assay as described previously (Lee H-Y et al. 2004 *BMC Infect Dis.* 4:12). Culture densities were measured spectrophotometrically at 600 nm then resuspended to a final concentration of $10^6$ CFU/ml. An A600 reading of 1 corresponds to $1.5 \times 10^9$ CFU/ml for the NTHi, $4.0 \times 10^8$ CFU/ml for *M. catarrhalis*, $1.0 \times 10^8$ CFU/ml for *S. pneumoniae*, and $2.5 \times 10^8$ CFU/ml for *E. coli*. The organisms were incubated with various concentrations of peptide at 37° C. with constant shaking for 1 h. Surviving microbes were plated in triplicate on trypticase soy broth plates (*E. coli*) or chocolate agar plate (NTHi, *M. catarrhalis*, and *S. pneumoniae*).

Immunohistochemistry has been carried out using human temporal bone sections using specific antibody raised against human SPAG11 (EP2E) synthetic peptide.

Results

Figure 12:
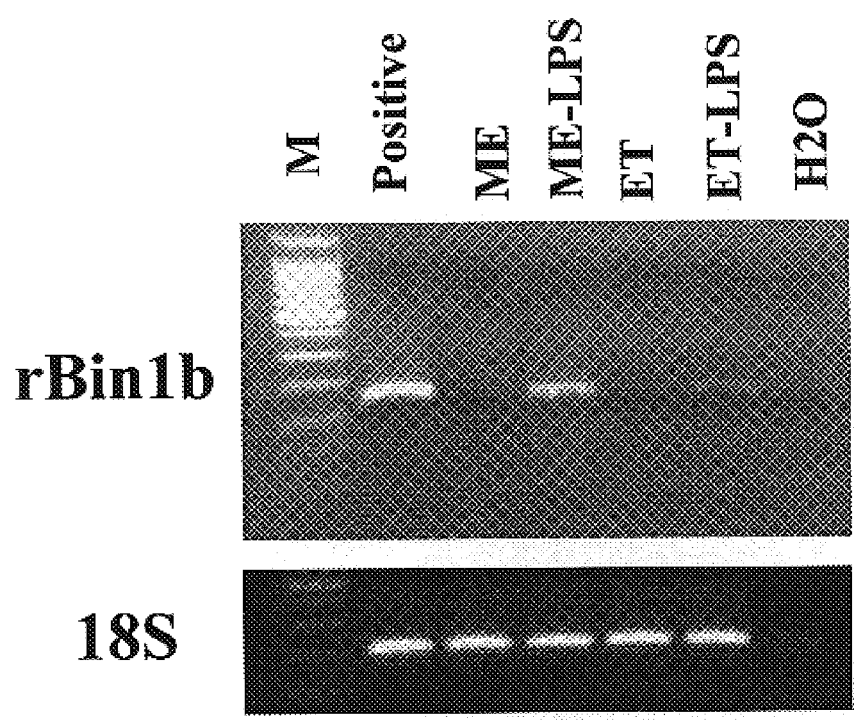
FIG. 12. Induction of rBin1b from rat tubotympanum upon Lipopolysaccharide challenge.
Figure 14:
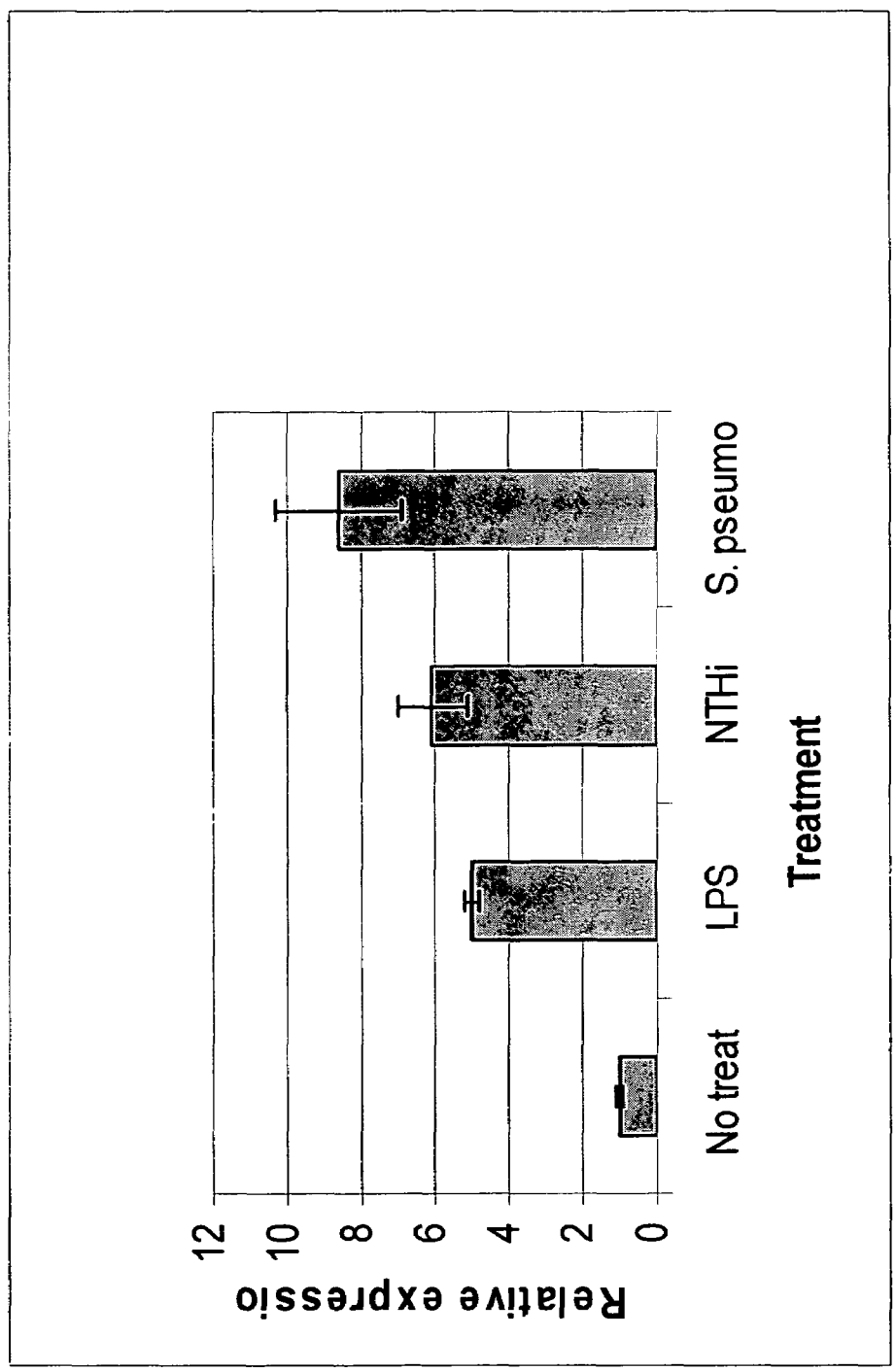
FIG. 14. Quantitative RT PCR analysis for induction of human SPAG11 (EP2E) from human middle ear epithelial cells HMEEC-1 upon otitis media pathogen challenge.

Rat Bin1b was expressed in the middle ear and E-tube (FIG. 12). In rat model, its expression was up regulated upon challenge of bacterial endotoxin LPS. Middle ear showed higher expression than e-tube. Quantitative PCR showed that more than 17,000 mRNA transcripts were produced per one million 18S RNA. Human SPAG11 (EP2E) expression was up-regulated upon challenge of OM pathogens (FIGS. 13 and 14). The sequence was confirmed from the PCR product.

Figure 15:
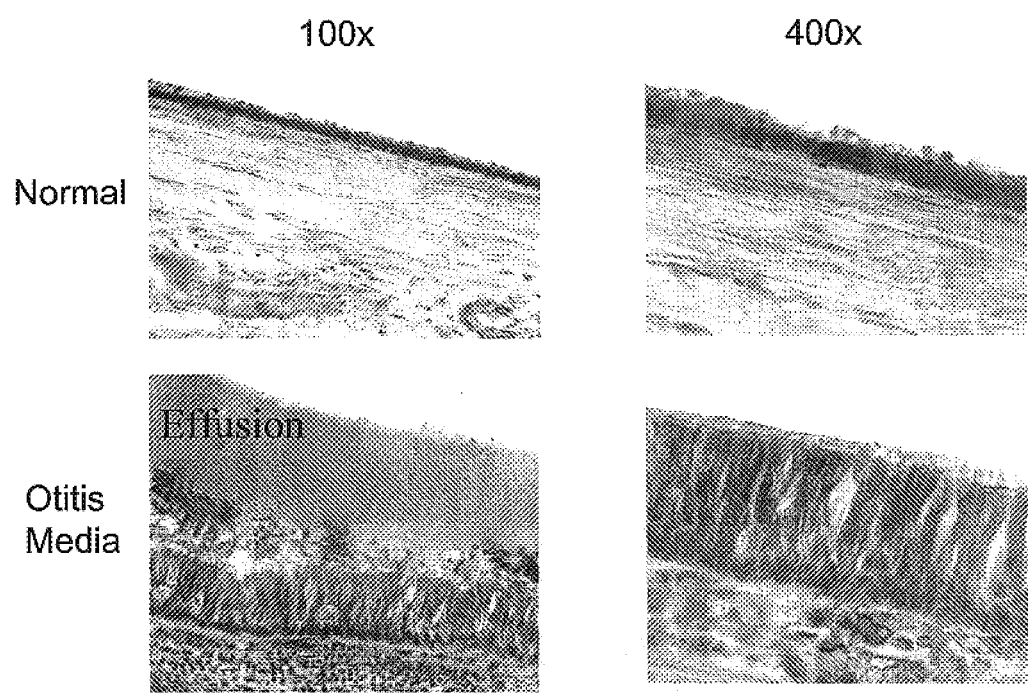
FIG. 15. Immunohistochemical detection of human SPAG11 (EP2E) on human archival temporal bone sections from otitis media patient.

Specific antibody was raised against synthetic human SPAG11 (EP2E) peptides and was used to detect SPAG11 (EP2E) in human achival temporal bones containing middle ear mucosal layer. SPAG11 (EP2E) peptide was detected in epithelial cells of human middle ear in OM patient (FIG. 15). Positive signal was found in the OM case, localized in apical and basal layers of epithelial cells. Effusion also showed positive signal.

Figure 16:
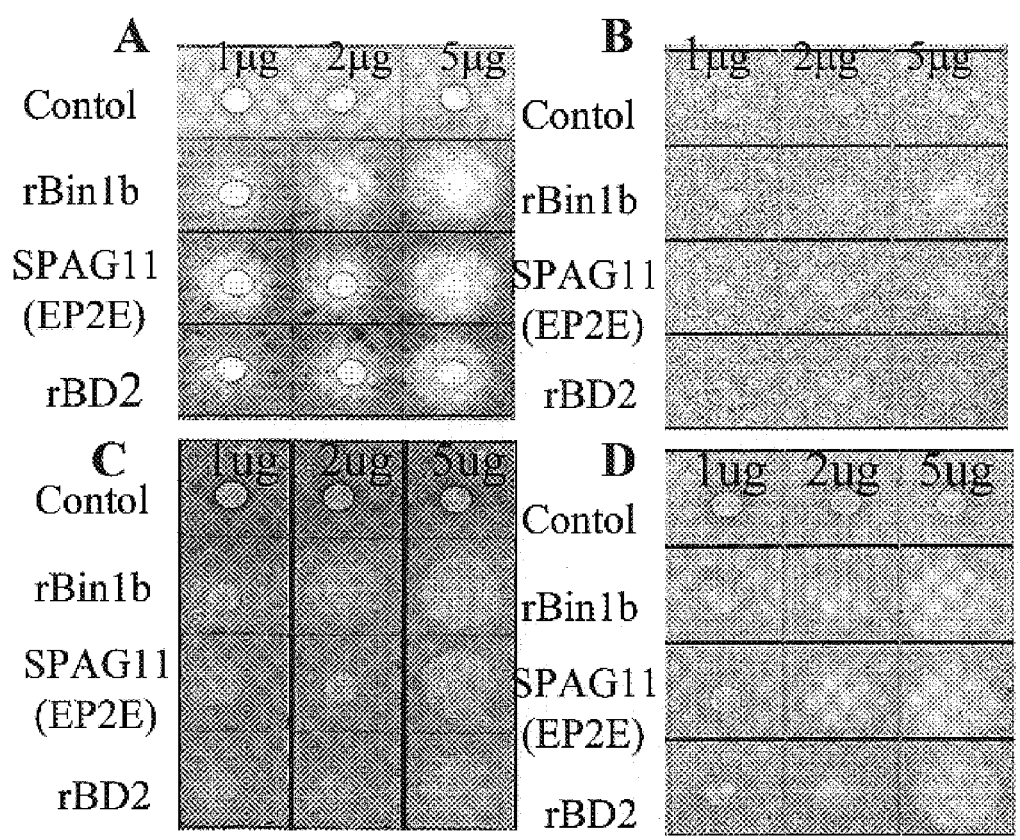
FIG. 16. Radial inhibition assay shows effect of rat Bin1b (SEQ ID NO: 42, GenBank Accession No. NP_659555) and human SPAG11 (EP2E) upon OM pathogens.
Figure 17:
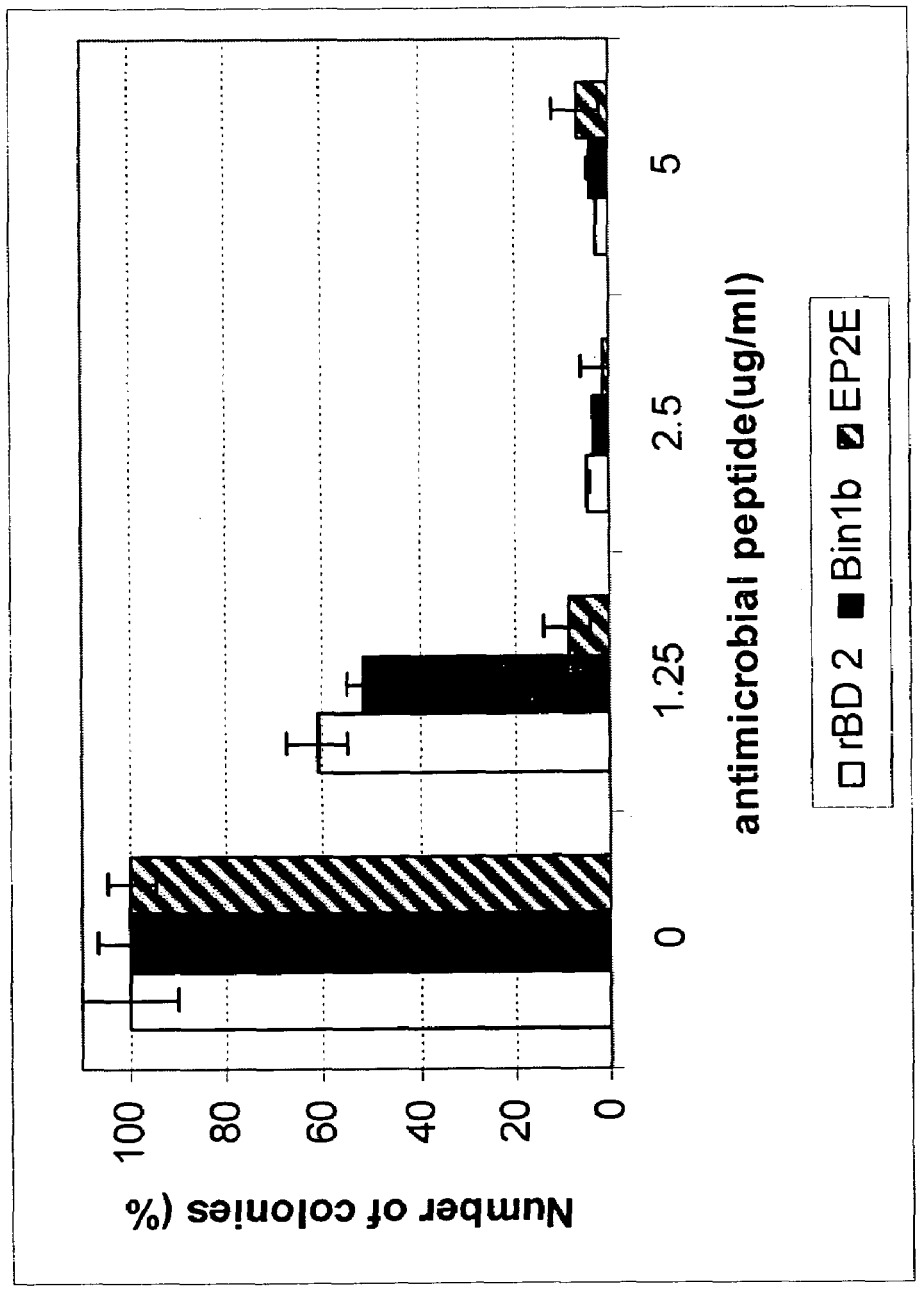
FIG. 17. Liquid broth assay shows the effect of rat Bin1b and human SPAG11 (EP2E) upon OM pathogen NTHi.
Figure 18:
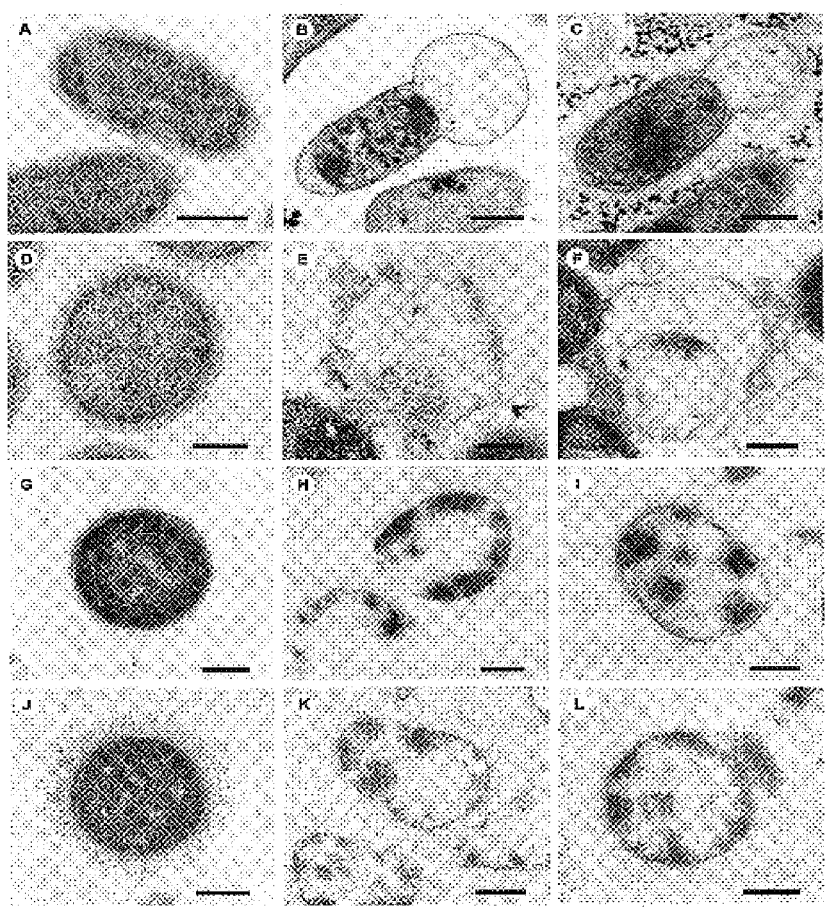
FIG. 18. Ultrastructural change in OM pathogens treated with rat Bin1b and human SPAG11 (EP2E).
Figure 19:
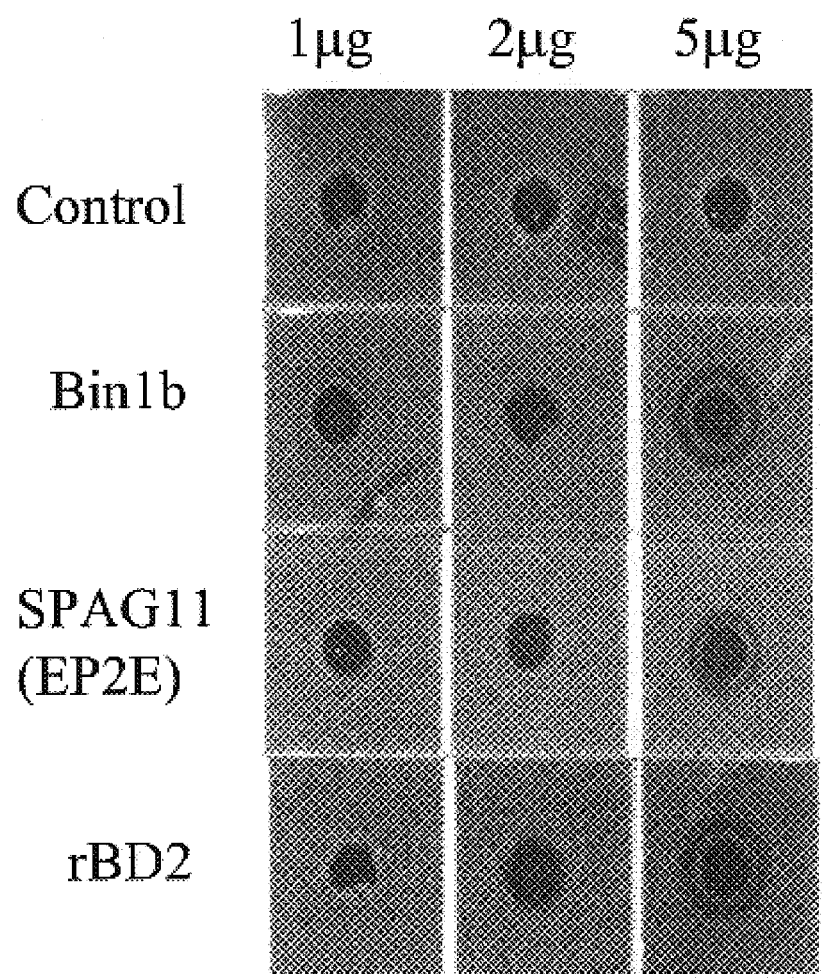
FIG. 19. Radial inhibition assay shows effect of rat Bin1b and human SPAG11 (EP2E) upon *E. coli* ML35.
Figure 20:
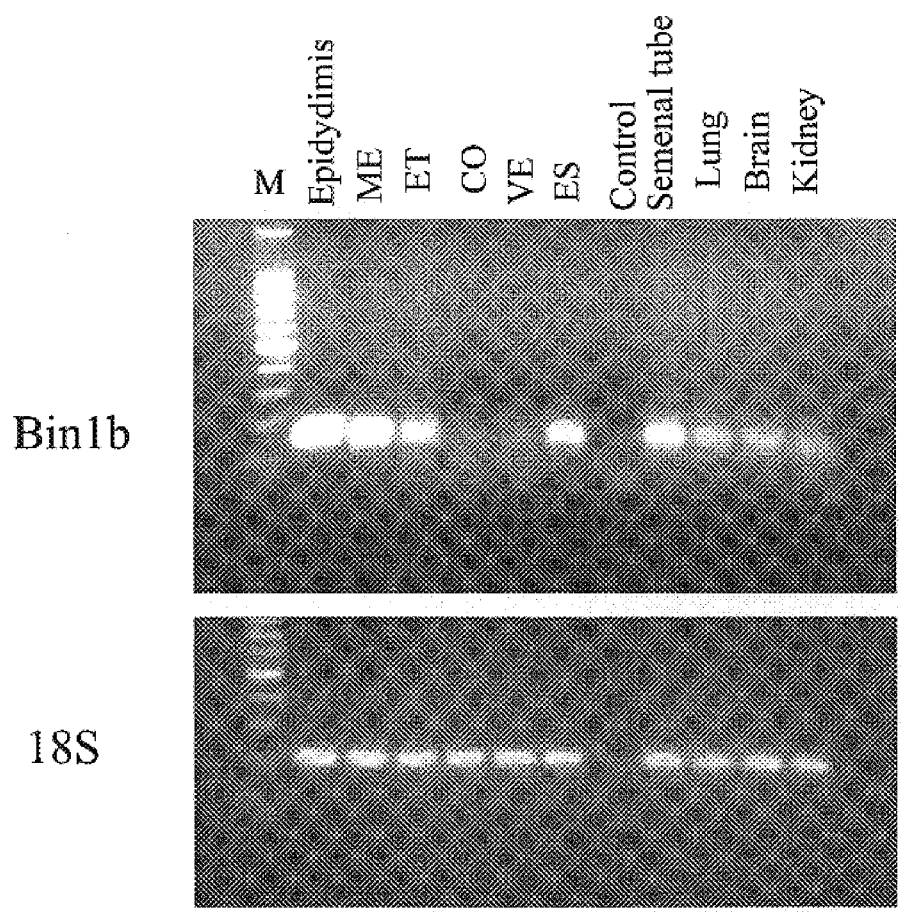
FIG. 20. Tissue specific expression of Rat Bin1b in the middle and inner ear.

Rat Bin1b and human SPAG11 (EP2E) peptides was synthesized chemically and refolded by oxidative refolding (Singh, R. R. & Rao, A. G. A. 2002 *Biochim Biophys Acta* 1597:280-291). Synthetic Bin1b inhibited the growth of *E. coli*, and OM pathogen *Moraxella* (FIG. 16 and FIG. 19) on radial assay. Their antimicrobial activity was confirmed in solution against OM pathogen NTHi (FIG. 17). Almost complete bactericidal activity was found in the 2.5-5.0 µg/ml concentration. Their antimicrobial activity was comparable to rat beta-defensin 2 which is one of potent antimicrobial molecules. Ultrastructural analysis (FIG. 18) showed that membrane structural changes occurred in the bacteria upon exposure to rat Bin1b and human SPAG11 (EP2E). The rat homologue of SPAG11 (EP2E), Bin1b, was expressed not only in middle ear and E-tube, but also in the inner ear endolymphatic sac (FIG. 20).

Thus, members of defensin family Bin1b in rat and SPAG11 (EP2E) in human were expressed in the middle ear and E-tube. Bin1b and SPAG11 (EP2E) were shown to be inducible peptides with limited tissue expression during bacterial infection. SPAG11 (EP2E) expression was up-regulated in OM in human temporal bone. Because it exhibits antimicrobial activity against OM pathogen, SPAG11 (EP2E) and its species variants are envisioned to serve as an innate defense against microbial invasion at specific mucosal surfaces of tubotympanum in the mammals, including rat and human.

Accordingly, in one preferred embodiment of the present invention, human SPAG11 (EP2E) synthetic peptide is used as a therapeutic agent against OM pathogens.

Moreover, innate immune molecules, such as lysozyrne, lactoferrin, beta-defensin 1, beta-defensin 2 and EP2E can be used to treat bacterial infections of the middle ear, sinuses, and meninges and are particularly effective against OM pathogens. Resulting in a new, innovative, and cost-effective approach to prevent and treat these diseases.

Although aspects of the present invention have been described in terms of certain preferred embodiments, other embodiments of the invention will become apparent to those of skill in the art in view of the disclosure herein. Thus, obvious changes and modifications may be made without departing from the spirit and scope of the invention. Accordingly, the scope of the invention is not intended to be limited by the foregoing, but rather to be defined only by the claims which follow.

All of the references cited herein are incorporated in their entirety by reference thereto.

What is claimed is:

1. A method for the treatment of microbial infections in a mammal comprising:
   administering to said mammal in need of said treatment a pharmaceutical composition comprising a defensin in an amount effective for the treatment of said microbial infections, thereby treating said microbial infections, wherein said microbial infections are caused by a microbe selected from the group consisting of NTHi strain 12, *M. catarrhalis*, *S. pneumoniae* serotype 3, and *S. pneumoniae* serotype 6B.

2. The method of claim 1, wherein said microbial infections are selected from the group consisting of otitis media, paranasal sinusitis, labyrinthitis and meningitis.

3. The method of claim 1, wherein said administering is orally, intranasally, or into the ear canal.

4. The method of claim 1, wherein said defensin is alpha-defensin or beta-defensin.

5. The method of claim 4, wherein said beta defensin is selected from the group consisting of beta-defensin 1, beta-defensin 2 and EP2E.

6. The method of claim 4, wherein said beta-defensin is EP2E.

7. The method of claim 1, wherein said pharmaceutical is administered at a dose of about 0.1 to 1000 mg/kg/day.

8. The method of claim 1, wherein said pharmaceutical is a solution or suspension.

9. The method of claim 1, wherein said pharmaceutical further comprises a salt chelator.

10. The method of claim 5, wherein said pharmaceutical further comprises lysozyme.

11. The method of claim 1, wherein said pharmaceutical composition comprises lysozyme, beta-defensin 1, beta-defensin 2, and EP2E.

12. The method of claim 1, wherein said mammal is a human.

13. The method of claim 1, wherein said mammal is an animal selected from the group consisting of: a dog, a cat, a horse, a ferret, a mouse, a rat and a cow.

14. A method for the treatment of microbial infections in a mammal comprising
administering to said mammal in need of said treatment a pharmaceutical composition comprising EP2E in an amount effective for the treatment of said microbial infections, thereby treating said microbial infections, wherein said microbial infections are caused by NTHi strain 12, *M. catarrhalis, S. Pneumoniae* serotype 3, and *S. pneumoniae* serotype 6B.

15. The method of claim 14, wherein said microbial infections are selected from the group consisting of otitis media, paranasal sinusitis, labyrinthitis and meningitis.

* * * * *

UNITED STATES PATENT AND TRADEMARK OFFICE
CERTIFICATE OF CORRECTION

| | | |
|---|---|---|
| PATENT NO. | : 7,338,936 B2 | Page 1 of 1 |
| APPLICATION NO. | : 10/971559 | |
| DATED | : March 4, 2008 | |
| INVENTOR(S) | : Lim et al. | |

It is certified that error appears in the above-identified patent and that said Letters Patent is hereby corrected as shown below:

Column 1, line 15 (i.e., after the first paragraph, and just before the header "Background of the Invention.") insert the following:

This invention was made with government support under Grant NIH NIDCD R01 DC05025 awarded by the National Institutes of Health. The government has certain rights in the invention.

Signed and Sealed this
Twenty-eighth Day of June, 2011

David J. Kappos
*Director of the United States Patent and Trademark Office*

SEQUENCE LISTING

```
<160> NUMBER OF SEQ ID NOS: 37

<210> SEQ ID NO 1
<211> LENGTH: 17
<212> TYPE: DNA
<213> ORGANISM: Artificial Sequence
<220> FEATURE:
<223> OTHER INFORMATION: synthetic primer

<400> SEQUENCE: 1 acttttttgtt gggcaat                                                17

<210> SEQ ID NO 2
<211> LENGTH: 17
<212> TYPE: DNA
<213> ORGANISM: Artificial Sequence
<220> FEATURE:
<223> OTHER INFORMATION: synthetic primer

<400> SEQUENCE: 2
aggctcatct gcctcag                                                 17

<210> SEQ ID NO 3
<211> LENGTH: 15
<212> TYPE: DNA
<213> ORGANISM: Artificial Sequence
<220> FEATURE:
<223> OTHER INFORMATION: synthetic primer

<400> SEQUENCE: 3
tctccgccag gcaca                                                   15

<210> SEQ ID NO 4
<211> LENGTH: 15
<212> TYPE: DNA
<213> ORGANISM: Artificial Sequence
<220> FEATURE:
<223> OTHER INFORMATION: synthetic primer

<400> SEQUENCE: 4
ggaggccgag gagca                                                   15

<210> SEQ ID NO 5
<211> LENGTH: 22
<212> TYPE: DNA
<213> ORGANISM: Artificial Sequence
<220> FEATURE:
```

-continued

<223> OTHER INFORMATION: synthetic primer

<400> SEQUENCE: 5
cgccatgaga acttcctacc tt                                    22

<210> SEQ ID NO 6
<211> LENGTH: 25
<212> TYPE: DNA
<213> ORGANISM: Artificial Sequence
<220> FEATURE:
<223> OTHER INFORMATION: synthetic primer

<400> SEQUENCE: 6
agttcatttc acttctgcgt cattt                                 25

<210> SEQ ID NO 7
<211> LENGTH: 25
<212> TYPE: DNA
<213> ORGANISM: Artificial Sequence
<220> FEATURE:
<223> OTHER INFORMATION: synthetic primer

<400> SEQUENCE: 7
gggtcttgta tctcctcttc tcgtt                                 25

<210> SEQ ID NO 8
<211> LENGTH: 25
<212> TYPE: DNA
<213> ORGANISM: Artificial Sequence
<220> FEATURE:
<223> OTHER INFORMATION: synthetic primer

<400> SEQUENCE: 8
tgcgtatctt tggacaccat agttt                                 25

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
cgggaaatcg tgcgtgacat                                       20

<210> SEQ ID NO 10
<211> LENGTH: 21
<212> TYPE: DNA
<213> ORGANISM: Artificial Sequence
<220> FEATURE:
<223> OTHER INFORMATION: synthetic primer

<400> SEQUENCE: 10
gcgtacaggt ctttgcggat g                                     21

<210> SEQ ID NO 11
<211> LENGTH: 34
<212> TYPE: PRT
<213> ORGANISM: Homo sapiens

<400> SEQUENCE: 11

Tyr Asn Cys Val Ser Ser Gly Gly Gln Cys Leu Tyr Ser Ala Cys Pro
 1               5                  10                  15

```
Ile Phe Thr Lys Ile Gln Gly Thr Cys Tyr Arg Gly Lys Ala Lys Cys
            20                  25                  30

Cys Lys
```

<210> SEQ ID NO 12
<211> LENGTH: 36
<212> TYPE: PRT
<213> ORGANISM: Homo sapiens

<400> SEQUENCE: 12

```
Val Thr Cys Leu Lys Ser Gly Ala Ile Cys His Pro Val Phe Cys Pro
 1               5                  10                  15

Arg Arg Tyr Lys Gln Ile Gly Thr Cys Gly Leu Pro Gly Thr Lys Cys
            20                  25                  30

Cys Lys Lys Pro
            35
```

<210> SEQ ID NO 13
<211> LENGTH: 26
<212> TYPE: PRT
<213> ORGANISM: Homo sapiens

<400> SEQUENCE: 13

```
Cys Val Leu Asn Val Cys Ser Thr Ser Leu Lys Gln Ile Gly Thr Tyr
 1               5                  10                  15

Gly His Asp Arg Ile Lys Cys Cys Lys Lys
            20                  25
```

<210> SEQ ID NO 14
<211> LENGTH: 37
<212> TYPE: PRT
<213> ORGANISM: Homo sapiens

<400> SEQUENCE: 14

```
Tyr Tyr Cys Arg Val Arg Gly Gly Arg Cys Ala Val Leu Ser Cys Leu
 1               5                  10                  15

Pro Lys Glu Glu Gln Ile Gly Lys Cys Ser Thr Arg Gly Arg Lys Cys
            20                  25                  30

Cys Arg Arg Lys Lys
            35
```

<210> SEQ ID NO 15
<211> LENGTH: 34
<212> TYPE: PRT
<213> ORGANISM: Homo sapiens

<400> SEQUENCE: 15

```
Arg Ile Cys Gly Tyr Gly Thr Ala Arg Cys Arg Lys Lys Cys Arg Ser
 1               5                  10                  15

Gln Glu Tyr Arg Ile Gly Arg Cys Pro Asn Thr Tyr Ala Cys Cys Leu
            20                  25                  30

Arg Lys
```

<210> SEQ ID NO 16
<211> LENGTH: 34
<212> TYPE: PRT
<213> ORGANISM: Homo sapiens

<400> SEQUENCE: 16

```
Glu Ser Cys Lys Leu Gly Arg Gly Lys Cys Arg Lys Glu Cys Leu Glu
 1               5                  10                  15
```

```
Asn Glu Lys Pro Asp Gly Asn Cys Arg Leu Asn Phe Leu Cys Cys Arg
            20                  25                  30

Gln Ile

<210> SEQ ID NO 17
<211> LENGTH: 37
<212> TYPE: PRT
<213> ORGANISM: Homo sapiens

<400> SEQUENCE: 17

Glu Lys Cys Asn Lys Leu Lys Gly Thr Cys Lys Asn Asn Cys Gly Lys
 1               5                  10                  15

Asn Glu Glu Leu Ile Ala Leu Cys Gln Lys Ser Leu Lys Cys Cys Arg
            20                  25                  30

Thr Ile Gln Pro Cys
        35

<210> SEQ ID NO 18
<211> LENGTH: 33
<212> TYPE: PRT
<213> ORGANISM: Homo sapiens

<400> SEQUENCE: 18

Thr Asn Cys Cys Glu Ala Glu Cys Leu Thr Phe Glu Val Lys Ile Gly
 1               5                  10                  15

Gly Cys Arg Ala Glu Leu Ala Pro Phe Cys Cys Lys Asn Arg Lys Lys
            20                  25                  30

His

<210> SEQ ID NO 19
<211> LENGTH: 37
<212> TYPE: PRT
<213> ORGANISM: Homo sapiens

<400> SEQUENCE: 19

Glu Ile Cys Glu Arg Pro Asn Gly Ser Cys Arg Asp Phe Cys Leu Glu
 1               5                  10                  15

Thr Glu Ile His Val Gly Arg Cys Leu Asn Ser Arg Pro Cys Cys Leu
            20                  25                  30

Pro Leu Gly His Gln
        35

<210> SEQ ID NO 20
<211> LENGTH: 38
<212> TYPE: PRT
<213> ORGANISM: Homo sapiens

<400> SEQUENCE: 20

Gly His Cys Leu Asn Leu Ser Gly Val Cys Arg Arg Asp Val Cys Lys
 1               5                  10                  15

Val Val Glu Asp Gln Ile Gly Ala Cys Arg Arg Arg Met Lys Cys Cys
            20                  25                  30

Arg Ala Trp Trp Ile Leu
        35

<210> SEQ ID NO 21
<211> LENGTH: 34
<212> TYPE: PRT
<213> ORGANISM: Homo sapiens
```

```
<400> SEQUENCE: 21

Val Asp Cys Arg Arg Ser Glu Gly Phe Cys Gln Glu Tyr Cys Asn Tyr
 1               5                  10                  15

Met Glu Thr Gln Val Gly Tyr Cys Ser Lys Lys Lys Asp Ala Cys Cys
                20                  25                  30

Leu His

<210> SEQ ID NO 22
<211> LENGTH: 39
<212> TYPE: PRT
<213> ORGANISM: Homo sapiens

<400> SEQUENCE: 22

Thr Ile Cys Arg Met Gln Gln Gly Ile Cys Arg Leu Glu Phe Cys His
 1               5                  10                  15

Ser Gly Glu Lys Lys Arg Asp Ile Cys Ser Asp Pro Trp Asn Arg Cys
                20                  25                  30

Cys Val Ser Asn Thr Asp Glu
                35

<210> SEQ ID NO 23
<211> LENGTH: 35
<212> TYPE: PRT
<213> ORGANISM: Homo sapiens

<400> SEQUENCE: 23

Asp Glu Cys Pro Ser Glu Tyr Tyr His Cys Arg Leu Lys Cys Asn Ala
 1               5                  10                  15

Asp Glu His Ala Ile Arg Tyr Cys Ala Asp Phe Ser Ile Cys Cys Lys
                20                  25                  30

Leu Lys Ile
        35

<210> SEQ ID NO 24
<211> LENGTH: 41
<212> TYPE: PRT
<213> ORGANISM: Homo sapiens

<400> SEQUENCE: 24

Gly Ile Gly Asp Pro Val Thr Cys Leu Lys Ser Gly Ala Ile Cys His
 1               5                  10                  15

Pro Val Phe Cys Pro Arg Arg Tyr Lys Gln Ile Gly Thr Cys Gly Leu
                20                  25                  30

Pro Gly Thr Lys Cys Cys Lys Lys Pro
        35                  40

<210> SEQ ID NO 25
<211> LENGTH: 36
<212> TYPE: PRT
<213> ORGANISM: Homo sapiens

<400> SEQUENCE: 25

Asp His Tyr Asn Cys Val Ser Ser Gly Gly Gln Cys Leu Tyr Ser Ala
 1               5                  10                  15

Cys Pro Ile Phe Thr Lys Ile Gln Gly Thr Cys Tyr Arg Gly Lys Ala
                20                  25                  30

Lys Cys Cys Lys
        35
```

<210> SEQ ID NO 26
<211> LENGTH: 37
<212> TYPE: PRT
<213> ORGANISM: Homo sapiens

<400> SEQUENCE: 26

Asn Ser Lys Arg Ala Cys Tyr Arg Glu Gly Glu Cys Leu Gln Arg
1               5                   10                  15
Cys Ile Gly Leu Phe His Lys Ile Gly Thr Cys Asn Phe Arg Phe Lys
            20                  25                  30
Cys Cys Lys Phe Gln
        35

<210> SEQ ID NO 27
<211> LENGTH: 35
<212> TYPE: PRT
<213> ORGANISM: Homo sapiens

<400> SEQUENCE: 27

Asn Glu Pro Val Ser Cys Ile Arg Asn Gly Gly Ile Cys Gln Tyr Arg
1               5                   10                  15
Cys Ile Gly Leu Arg His Lys Ile Gly Thr Cys Gly Ser Pro Phe Lys
            20                  25                  30
Cys Cys Lys
        35

<210> SEQ ID NO 28
<211> LENGTH: 45
<212> TYPE: PRT
<213> ORGANISM: Homo sapiens

<400> SEQUENCE: 28

Gly Ile Ile Asn Thr Leu Gln Lys Tyr Tyr Cys Arg Val Arg Gly Gly
1               5                   10                  15
Arg Cys Ala Val Leu Ser Cys Leu Pro Lys Glu Glu Gln Ile Gly Lys
            20                  25                  30
Cys Ser Thr Arg Gly Arg Lys Cys Cys Arg Arg Lys Lys
        35                  40                  45

<210> SEQ ID NO 29
<211> LENGTH: 50
<212> TYPE: PRT
<213> ORGANISM: Homo sapiens

<400> SEQUENCE: 29

Glu Phe Glu Leu Asp Arg Ile Cys Gly Tyr Gly Thr Ala Arg Cys Arg
1               5                   10                  15
Lys Lys Cys Arg Ser Gln Glu Tyr Arg Ile Gly Arg Cys Pro Asn Thr
            20                  25                  30
Tyr Ala Cys Cys Leu Arg Lys Trp Asp Glu Ser Leu Leu Asn Arg Thr
        35                  40                  45
Lys Pro
    50

<210> SEQ ID NO 30
<211> LENGTH: 37
<212> TYPE: PRT
<213> ORGANISM: Homo sapiens

```
<400> SEQUENCE: 30

Asp Gln Tyr Lys Cys Leu Gln His Gly Gly Phe Cys Leu Arg Ser Ser
1               5                   10                  15

Cys Pro Ser Asn Thr Lys Leu Gln Gly Thr Cys Lys Pro Asp Lys Pro
            20                  25                  30

Asn Cys Cys Lys Ser
            35

<210> SEQ ID NO 31
<211> LENGTH: 40
<212> TYPE: PRT
<213> ORGANISM: Homo sapiens

<400> SEQUENCE: 31

Ala Glu Leu Asp His Cys His Thr Asn Gly Gly Tyr Cys Val Arg Ala
1               5                   10                  15

Ile Cys Pro Pro Ser Ala Arg Arg Pro Gly Ser Cys Phe Pro Glu Lys
            20                  25                  30

Asn Pro Cys Cys Lys Tyr Met Lys
            35                  40

<210> SEQ ID NO 32
<211> LENGTH: 39
<212> TYPE: PRT
<213> ORGANISM: Homo sapiens

<400> SEQUENCE: 32

Ile Asn Asn Pro Val Ser Cys Leu Arg Lys Gly Gly Arg Cys Trp Asn
1               5                   10                  15

Arg Cys Ile Gly Asn Thr Arg Gln Ile Gly Ser Cys Gly Val Pro Phe
            20                  25                  30

Leu Lys Cys Cys Lys Arg Lys
            35

<210> SEQ ID NO 33
<211> LENGTH: 39
<212> TYPE: PRT
<213> ORGANISM: Homo sapiens

<400> SEQUENCE: 33

Ile Asn Asn Pro Ile Thr Cys Met Thr Asn Gly Ala Ile Cys Trp Gly
1               5                   10                  15

Pro Cys Pro Thr Ala Phe Arg Gln Ile Gly Asn Cys Gly His Phe Lys
            20                  25                  30

Val Arg Cys Cys Lys Ile Arg
            35

<210> SEQ ID NO 34
<211> LENGTH: 39
<212> TYPE: PRT
<213> ORGANISM: Homo sapiens

<400> SEQUENCE: 34

Gly Asn Pro Val Ser Cys Val Arg Asn Lys Gly Ile Cys Val Pro Ile
1               5                   10                  15

Arg Cys Pro Gly Ser Met Lys Gln Ile Gly Thr Cys Val Gly Arg Ala
            20                  25                  30

Val Lys Cys Cys Arg Lys Lys
            35
```

```
<210> SEQ ID NO 35
<211> LENGTH: 38
<212> TYPE: PRT
<213> ORGANISM: Homo sapiens

<400> SEQUENCE: 35

Asp Phe Ala Ser Cys His Thr Asn Gly Gly Ile Cys Leu Pro Asn Arg
 1               5                  10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 36
<211> LENGTH: 38
<212> TYPE: PRT
<213> ORGANISM: Homo sapiens

<400> SEQUENCE: 36

Asn His Val Thr Cys Arg Ile Asn Arg Gly Phe Cys Val Pro Ile Arg
 1               5                  10                  15

Cys Pro Gly Arg Thr Arg Gln Ile Gly Thr Cys Phe Gly Pro Arg Ile
            20                  25                  30

Lys Cys Cys Arg Ser Trp
        35

<210> SEQ ID NO 37
<211> LENGTH: 38
<212> TYPE: PRT
<213> ORGANISM: Homo sapiens

<400> SEQUENCE: 37

Gly Pro Leu Ser Cys Gly Arg Asn Gly Gly Val Cys Ile Pro Ile Arg
 1               5                  10                  15

Cys Pro Val Pro Met Arg Gln Ile Gly Thr Cys Phe Gly Arg Pro Val
            20                  25                  30

Lys Cys Cys Arg Ser Trp
        35
```